US009198895B2

(12) United States Patent
Heaton et al.

(10) Patent No.: US 9,198,895 B2
(45) Date of Patent: Dec. 1, 2015

(54) CHROMAN DERIVATIVES, MEDICAMENTS AND USE IN THERAPY

(71) Applicant: MEI Pharma, Inc., San Diego, CA (US)

(72) Inventors: Andrew Heaton, Abbotsford (AU); Alan Husband, McMahon's Point (AU)

(73) Assignee: MEI Pharma, Inc., San Diego, CA (US)

( * ) Notice: Subject to any disclaimer, the term of this patent is extended or adjusted under 35 U.S.C. 154(b) by 0 days.

(21) Appl. No.: 14/589,941

(22) Filed: Jan. 5, 2015

(65) Prior Publication Data
US 2015/0238458 A1 Aug. 27, 2015

Related U.S. Application Data

(60) Continuation of application No. 13/891,975, filed on May 10, 2013, now Pat. No. 8,957,109, which is a continuation of application No. 13/415,697, filed on Mar. 8, 2012, now Pat. No. 8,461,361, which is a continuation of application No. 13/231,794, filed on Sep. 13, 2011, now Pat. No. 8,163,795, which is a division of application No. 11/230,505, filed on Sep. 21, 2005, now Pat. No. 8,080,675.

(60) Provisional application No. 60/611,299, filed on Sep. 21, 2004, provisional application No. 60/676,934, filed on May 3, 2005.

(30) Foreign Application Priority Data

Oct. 29, 2004 (JP) .................................. 2004-315009
Nov. 5, 2004 (AU) ............................... 2004-906363
Nov. 19, 2004 (WO) ................ PCT/AU2004/001619

(51) Int. Cl.
A61K 31/35 (2006.01)
A61K 31/353 (2006.01)
A61K 33/24 (2006.01)
A61K 31/7068 (2006.01)
A61K 31/337 (2006.01)
A61K 31/282 (2006.01)
A61K 31/655 (2006.01)
A61K 41/00 (2006.01)
A61K 31/37 (2006.01)

(52) U.S. Cl.
CPC ............. *A61K 31/353* (2013.01); *A61K 31/282* (2013.01); *A61K 31/337* (2013.01); *A61K 31/37* (2013.01); *A61K 31/655* (2013.01); *A61K 31/7068* (2013.01); *A61K 33/24* (2013.01); *A61K 41/0038* (2013.01)

(58) Field of Classification Search
CPC ...................................................... A61K 31/37
USPC ....................................................... 549/399
See application file for complete search history.

(56) References Cited

U.S. PATENT DOCUMENTS

| 3,340,276 A | 9/1967 | Carney |
| 3,471,520 A | 10/1969 | Irmscher et al. |
| 3,535,344 A | 10/1970 | Irmscher |
| 4,157,984 A | 6/1979 | Zilliken |
| 4,218,489 A | 8/1980 | Zilliken |
| 4,232,122 A | 11/1980 | Zilliken |
| 4,234,577 A | 11/1980 | Zilliken |
| 4,366,082 A | 12/1982 | Zilliken |
| 4,366,248 A | 12/1982 | Zilliken |
| 4,368,264 A | 1/1983 | Zilliken |
| 4,390,559 A | 6/1983 | Zilliken |
| 4,447,622 A | 5/1984 | Salman et al. |
| 4,644,012 A | 2/1987 | Tsuda et al. |
| 4,814,346 A | 3/1989 | Albert et al. |
| 5,059,609 A | 10/1991 | Eggler et al. |
| 5,134,127 A | 7/1992 | Stella et al. |
| 5,280,040 A | 1/1994 | Labroo et al. |
| 5,389,646 A | 2/1995 | Labroo |
| 5,464,862 A | 11/1995 | Labroo et al. |
| 5,696,149 A | 12/1997 | Korsgaard et al. |
| 5,726,202 A | 3/1998 | Shalmi et al. |
| 5,756,539 A | 5/1998 | Skrumsager et al. |
| 5,780,503 A | 7/1998 | Biftu et al. |
| 5,849,461 A | 12/1998 | Hatakeyama et al. |
| 5,883,118 A | 3/1999 | Shalmi et al. |
| 5,919,817 A | 7/1999 | Jacobsen et al. |
| 5,958,967 A | 9/1999 | Jacobsen et al. |
| 5,985,306 A | 11/1999 | Jacobsen et al. |
| 5,994,390 A | 11/1999 | Jacobsen et al. |
| 5,998,451 A | 12/1999 | Eggler et al. |
| 6,005,003 A | 12/1999 | Nique |
| 6,043,269 A | 3/2000 | Jacobsen et al. |
| 6,316,494 B1 | 11/2001 | Jacobsen et al. |
| 6,610,733 B2 | 8/2003 | Park et al. |
| 6,645,951 B1 | 11/2003 | Jo et al. |
| 6,649,648 B1 | 11/2003 | Kelly et al. |

(Continued)

FOREIGN PATENT DOCUMENTS

| CA | 2581316 | 3/2006 |
| EP | 0267155 | 10/1987 |

(Continued)

OTHER PUBLICATIONS

U.S. Appl. No. 60/611,299, filed Sep. 21, 2004, Heaton.

(Continued)

Primary Examiner — Andrew D Kosar
Assistant Examiner — Raymond Covington
(74) Attorney, Agent, or Firm — Wilson Sonsini Goodrich & Rosati

(57) ABSTRACT

Novel chroman derivatives and intermediate compounds, compositions containing same, methods for their preparation and uses thereof as therapeutic agents particularly as anti-cancer and chemotherapeutic selective agents are described.

10 Claims, 13 Drawing Sheets

(56) References Cited

U.S. PATENT DOCUMENTS

| | | |
|---|---|---|
| 7,056,952 B1 | 6/2006 | Joannon |
| 7,202,273 B2 | 4/2007 | Kelly et al. |
| 7,601,855 B2 | 10/2009 | Heaton |
| 8,080,675 B2 | 12/2011 | Heaton et al. |
| 8,084,628 B2 | 12/2011 | Heaton et al. |
| 8,163,795 B2 | 4/2012 | Heaton et al. |
| 8,461,361 B2 | 6/2013 | Heaton et al. |
| 8,697,891 B2 | 4/2014 | Heaton et al. |
| 8,957,109 B2 | 2/2015 | Heaton et al. |
| 2006/0074126 A1 | 4/2006 | Heaton et al. |
| 2006/0074127 A1 | 4/2006 | Heaton et al. |
| 2009/0317490 A1 | 12/2009 | Heaton |
| 2010/0173983 A1 | 7/2010 | Brown et al. |
| 2012/0004296 A1 | 1/2012 | Heaton et al. |
| 2012/0039917 A1 | 2/2012 | Husband et al. |
| 2012/0114766 A1 | 5/2012 | Heaton et al. |
| 2012/0172424 A1 | 7/2012 | Heaton et al. |
| 2014/0161908 A1 | 6/2014 | Heaton et al. |
| 2014/0170243 A1 | 6/2014 | Heaton et al. |

FOREIGN PATENT DOCUMENTS

| | | |
|---|---|---|
| EP | 0313295 | 4/1989 |
| EP | 0470310 | 12/1992 |
| EP | 0955286 | 11/1999 |
| GB | 1433013 | 4/1976 |
| JP | 2000-506507 | 5/2000 |
| JP | 2001-502706 | 2/2001 |
| JP | 2001-502711 | 2/2001 |
| JP | 2006-96734 | 4/2006 |
| JP | 2012-144537 | 8/2012 |
| JP | 2014-237638 | 12/2014 |
| WO | WO-80/02098 A1 | 10/1980 |
| WO | WO-94/08986 A1 | 4/1994 |
| WO | WO-94/20099 A1 | 9/1994 |
| WO | WO-96/21442 A1 | 7/1996 |
| WO | WO-96/21443 A1 | 7/1996 |
| WO | WO-96/21444 A1 | 7/1996 |
| WO | WO-96/22091 A1 | 7/1996 |
| WO | WO-96/22092 A1 | 7/1996 |
| WO | WO-96/22093 A1 | 7/1996 |
| WO | WO-97/25035 A1 | 7/1997 |
| WO | WO-97/25036 A1 | 7/1997 |
| WO | WO-97/25037 | 7/1997 |
| WO | WO-97/25038 A1 | 7/1997 |
| WO | WO-98/02154 A1 | 1/1998 |
| WO | WO-98/02156 A1 | 1/1998 |
| WO | WO-98/08503 A1 | 3/1998 |
| WO | WO-98/17662 A1 | 4/1998 |
| WO | WO-98/18770 A1 | 5/1998 |
| WO | WO-98/18771 A1 | 5/1998 |
| WO | WO-98/18772 A1 | 5/1998 |
| WO | WO-98/18773 A1 | 5/1998 |
| WO | WO 98/18774 A1 | 5/1998 |
| WO | WO-98/18775 A1 | 5/1998 |
| WO | WO-98/18776 A1 | 5/1998 |
| WO | WO-98/18778 A1 | 5/1998 |
| WO | WO 98/18779 A1 | 5/1998 |
| WO | WO-98/25916 A1 | 6/1998 |
| WO | WO-98/32437 A1 | 7/1998 |
| WO | WO-98/33499 A1 | 8/1998 |
| WO | WO-98/33500 A1 | 8/1998 |
| WO | WO-99/49862 A1 | 10/1999 |
| WO | WO-99/55898 A1 | 11/1999 |
| WO | WO-99/63974 A2 | 12/1999 |
| WO | WO-99/65893 A1 | 12/1999 |
| WO | WO-00/49009 | 8/2000 |
| WO | WO-00/66576 A1 | 11/2000 |
| WO | WO-01/17986 A1 | 3/2001 |
| WO | WO-01/26651 A2 | 4/2001 |
| WO | WO-01/54699 A1 | 8/2001 |
| WO | WO-02/02548 A1 | 1/2002 |
| WO | WO-02/059113 A1 | 8/2002 |
| WO | WO-03/016270 A2 | 2/2003 |
| WO | WO-03/035635 A1 | 5/2003 |
| WO | WO-03/063859 A1 | 8/2003 |
| WO | WO-03/086386 A1 | 10/2003 |
| WO | WO-2004/030662 A1 | 4/2004 |
| WO | WO-2005/049008 A1 | 6/2005 |
| WO | WO-2006/032085 A1 | 3/2006 |
| WO | WO-2006/032086 A1 | 3/2006 |
| WO | WO-2008/113100 | 9/2008 |
| WO | WO-2010/022467 | 4/2010 |

OTHER PUBLICATIONS

JP Patent Application No. 2014-014217 Office Action dated Feb. 19, 2015 (with translation).
Abegaz, et al., Isoflavonoids from the roots of Salsola somalensis. Phytochemistry. 1991; 30(4):1281-4 (Abstract Only in English).
Agarwal, et al., Phenolic constituents of Iris Milesii rhizomes, Phytochemistry (Elsevier) 1984; 23(6):1342-3 (Abstract Only in English).
Agarwal, et al., Isoflavones of two Iris species. Phytochemistry (Elsevier) 1984; 23(11):2703-4 (Abstract Only in English).
Aggarwal, et al., From chemoprevention to chemotherapy: common targets and common goals. Expert Opin. Investig. Drugs. 2004;13(10):1327-38.
Akimoto, et al., Genistein, a tyrosine kinase inhibitor, enhanced radiosensitivity in human esophageal cancer cell lines in vitro: possible involvement of inhibition of survival signal transduction pathways. Int. J. Radiation Oncology Biol. Phys. 2001; 50(1):195-201.
ALDRICH Handbook of Fine Chemicals and Laboratory Equipment © 2002, Sigma-Aldrich Pty Limited, Australia: Note: Sigma-Aldrich is a US Company, catalogue/handbook from which the pages derive from is the AU publication.
Antus, et al., Synthesis of some pterocarpenes obtained from Brya ebenus, J. Chem. Soc., Perkin Trans. 1982;6:1389-94 (Abstract Only in English).
Arnone, et al., Isoflavonoid constituents of the West African red wood, Baphia nitida. Phtyochemistry. 1981; 20(4):799-801 (Abstract Only in English).
Bellisarii, et al., Tumor necrosis factor-α and cardiovascular diseases. Ital Heart J. 2001;2(6):408-17.
Bezuidenhoudt et al., Synthesis of Isoflavanoid Oligomers Using a Pterocarpan as Inceptive Electrophile. J Chem Soc Parkin Trans. 1984; 1:2767-78.
Bradbury, Some oestrogenic 4-phenyl-substituted isoflav-3-ENS, Aust J Chem. 1953;6:447-49.
Briviba, et al., Isoflavonoids as inhibitors of lipid peroxidation and quenchers of singlet oxygen. Antioxidants in Health and Disease, 7(Flavonoids in Health and Disease). 1998:295-302 (Abstract Only in English).
Bury, et al., Synthesis and pharmacological evaluation of novel cis-3,4-diaryl-hydroxychromanes as high affinity partial agonists for the estrogen receptor. Bioorg Med Chem. 2002;10:125-145.
Caltagirone, et al., Flavanoids apigenin and quercetin inhibit melanoma growth and metastatic potential. Int J Cancer Suppl. 2002; 87(4):595-600 (Abstract Only in English).
Caltagirone, et al., Interaction with type II estrogen binding sites and antiproliferative activity of tamoxifen and quercetin in human non-small-cell lung cancer, American Journal of Respiratory Cell and Molecular Biology. Jul. 1997; 17:(1):51-9 (Abstract Only in English).
Constantinou, et al. Phenoxodiol (2H-1-Benzopyran-7-0, 1, 3-(4-hydroxyphenyl), a Novel Isoflavone Derivative, Inhibits DNA Topoisomerase II by Stabilizing the Cleavable Complex. Anticancer Research. 2002;22:2581-86.
Constantinou, et al., Phenoxodiol, a novel isofavone derivative, inhibits dimethylbenz[a]anthracene(DMBA)-induced mammary carcinogenesis in female Sprague—Dawley rats. Eur J Cancer. 2003; 39:1012-18.
De Vincenzo, et al.,Flavanoids and negative control of cell proliferation in ovarian tumors. Acta Medica Romana. 1992; 30(1-2):126-32 (Abstract Only in English).
Dorai, et al , Role of chemopreventive agents in cancer therapy. Cancer Lett. 2004; 215:129-40.
EP 05779877.9 Search Report dated Apr. 28, 2009.

(56) References Cited

OTHER PUBLICATIONS

EP 05787045.3 Search Report dated Oct. 7, 2008.
EP 11180383.9 Office Action dated Mar. 25, 2014.
Fukui, et al., The synthesis of irisolone, Bull. Chem. Soc. Japan. 1965; 38(6):887-93 (Abstract Only in English).
Gamble, et al., Phenoxodiol, an experimental anticancer drug, shows potent antiangiogenic properties in addition to its antitumour effects. Int. J. Cancer. 2006; 118:2412-20.
Giacomelli. et al., Silybin and its bioavailable, phospholipid complex(IdB 1016) potentiate in vitro and in vivo the activity of cisplatin. Life Sciences. Feb. 8, 2002; 70(12):1447-59 (Abstract Only in English).
Gupta et al., The use of Friedel-Crafts reactions for the synthesis of deoxybenzoins. Indian J Chem. 1968; 6(9):481-4 (Abstract Only in English).
Hem Chandra Jha, et al., Carbon-13—chemical shift assignments of chromones and isoflavones. Can J Chem. 1980; 58:1211-19.
Hersey, et al., How melanoma cells evade trail-induced apoptosis. Nat Rev Cancer. Nov. 2001; 1(2)142-50.
Horie, et al.,Studies of the selective O-alkylation and dealkylation of flavonoids. XX. A convenient method for synthesizing 5,6,7-trihydroxyisoflavones and 5,6-dihydroxy-7-methoxyisoflavones. Pharm Bull. 1996; 44(3):486-91 (Abstract Only in English).
Hu et al., Drug Metabolism and Dispostion, 31(7):924-931 (2003).
Ito, et al., Isoflavonoids from Belamcanda chinensis. Pharm Bull. 2001; 49(9):1229-31 (Abstract Only in English).
Kakeji, et al., Preclinical studies of the combination of angiogenic inhibitors with cytotoxic agents. Invest New Drugs. 1997; 15:39-48.
Kamsteeg, et al., Phenoxodiol—an isoflavone analog—induces apoptosis in chemoresistant ovarian cancer cells. Oncogene. 2003; 22:2611-20.
Kang, et al., "Scientific Analysis of Formulation Theory of Chungpesagan-tang; In vitro Cytotoxicity of Cisplatin Combined with Chungpesagan-tang", Natural Product Sciences, vol. 6(4), pp. 165-169, (2000).
Kanzawa, et al. Int. J. Cancer 71, 311-319 (1997).
Khoshyomn, et al., Synergistic Action of Genistein and Ciplatin on Growth Inhibition and Cytotoxicity of Human Medulloblastoma Cells. Pediatr Neurosurg. 2000; 33:123-31.
Kinjo, et al., Novel santalin analogs from Pterpcarpus santalinus (leguminosae): their biogenesis and anti-oxidative activities. Tennen Yuki Kagobutsu Toronkai Koen Yoshishu. 1995; 37:493-8 (Abstract Only in English).
Klus, et al., Formation of polyhydroxylated isoflavones from the soybean seed isoflavones daidzein and glycitein by bacteria isolated from tempe. Arch Microbiol. 1995; 164(6):428-34 (Abstract Only in English).
Kothari, et al. Inhibition of cholesterol ester trnasfer protein by CGS 25159 and changes in lipoproteins in hamsters: Atherosclerosis. (Shannon, Ireland) 1997; 128(1):59-66.
Kulling, et al., Oxidative metabolism of the soy isoflavones daidzein and genistein in humans in vitro and in vivo. J Agric Food Chem. 2001; 49(6):3024-33 (Abstract Only in English).
Lawson, Estrogenic activity of some derivatives of isoflaven and isoflavanol. J Chem Soc. 1954:4448-50 (Abstract Only in English).
Lei, et al., Enhancement of Chemosensitivity and Programmed Cell death by Tyrosine Kinase Inhibitors Correlates with EGFR Expression in Non-Small Cell Lung Cancer Cells. Anticancer Res. 1989; 19:221-28.
Li, et al., Apoptosis-Inducing Effect of Chemotherapeutic Agents Is Potentiated by Soy Isoflavone Genistein, a Natural Inhibitor of NF-KB in BxPC-3 Pancreatic Cancer Cell Line. Pancreas. 2004; (28)4:e90-5.
Mani, et al, Isoflavones. III. Nitration of 7,8- and 6,7-dihydroxyisoflavones and their methyl ether. J Inst Chem. 1971; 43(6):234-40 (Abstract Only in English).
Mani, et al., Isoflavones. I. Bromination of isoflavones. J Inst Chem. 1974; 46(Pt.3):61-5 (Abstract Only in English).
Mansour, et al., Enhancement of Chemotherapeutic Efficacy by Combining Agents that Block IL-10 in CLL Cell Lines. New Jersey Medical School, UMDNJ, Newark, NJ, USA Blood. Nov. 16, 2002; 100(11) Abstract No. 4997. Print (Abstract Only in English).
McDonnell, et al., Improvement in Efficacy of Chemoradiotherapy by Addition of and Antiangiogenic Agent in a Murine Tumor Model. J Surg Res. 2004; 116:19-23.
Micheli, et al., "Coumestro, Plant Phenolics, and Synthetic Estrogens: a Correlation of Structure and Activity", Journal of Medicinal and Pharmaceutical Chemistry, vol. 5, 1962, pp. 321-335.
Montandon, et al., In-vitro versus in-vivo activities of new 5-lipoxygenase inhibitors with anti-inflammatory activity, Int J Tissue React. 1989; 11(3); 107-12 (Abstract Only in English).
Nakata et al., C225 Antiepidermal Growth Factor Receptor Antibody Enhances the Efficacy of Docetaxel Chemoradiotherapy. Int J Radiation Oncology Biol Phys. 2004; 59(4): 1163-73.
Neelam, et al., Combination of flavone acetic acid (FAA) with adriamycin, cis-platinum and diflouoromethylornithine (DFMO) in vitro against human colon cancer cells. Invest New Drugs. Aug. 1990; 8(3):263-8 (Abstract Only in English).
O'Dwyer, et al., Antitumor Activity and Biochemical Effects of Aphidicolin Glycinate(NSC 303812) Alone and in Combination with Cisplatin in Vivo. Cancer Res. Feb. 1, 1994; 54:724-29.
O'Neill, et al., Inducible Isoflavonoids from the Lima Bean, Phaseolus lunatus. Phytochemistry. 1986; 25(6): 1315-22.
PCT AU2005/01435 ISR dated Dec. 21, 2005.
PCT AU2005/001436 ISR dated Dec. 21, 2005.
PCT AU2004/001619 ISR dated Feb. 2, 2005.
Rafi, et al., Modulation of bcl-2 and Cytotoxicity by Licochalcone-A, a Novel Estrogenic Flavonoid. Anticancer Res. 2000; 20:2653-58.
Ravindranath, et al., Anticancer Therapeutic Potential of Soy Isoflavone, Genistein. Complementary and Alternative Approaches to Biomedicine, edited by Edwin L. Cooper and Nobuo Yamaguchi. Kluwer Academic/Plenum Publishers. 2004; 121.
Registration No. 1157-39-7, 4H-1-Benzopyran-4-one, 7-methoxy-3-(4- methoxyphenyl)-methyl-(9CI), Nov. 16, 1984.
Registration No. 116703-40-3, 4H-1-Benzopyran-4-one, 2,3-dihydro-7,8-dimethoxy-3-(4-methoxyphenyl)-(9CI), Oct. 2, 1988.
Registration No. 116703-49-2, 4H-1-Benzopyran-4-one, 2,3-dihydro-7,8-dihydroxy-3-(4-methoxyphenyl)-(9CI), Oct. 2, 1988.
Registration No. 116718-51-5, 4H-1-Benzopyran-4-one, 7-hydroxy-3-(4-methoxyphenyl)-8-methyl-methyl-(9CI), Oct. 2, 1988.
Registration No. 124093-18-1, 4H-1-Benzopyran-4-one, 2,3-dihydro-7-hydroxy-3-(4-hydroxy-3-methoxyphenyl)-(9CI), Dec. 1, 1989.
Registration No. 129159-04-2, 4H-1-Benzopyran-4-one, 2,3-dihydro-3-(4-hydroxyphenyl)-(9CI), Aug. 31, 1990.
Registration No. 129159-05-3, 4H-1-Benzopyran-4-one, 3-(3,4-dihydroxyphenyl)-2,3-dihydro-(9CI), Aug. 31, 1990.
Registration No. 13139-86-1, Magnesium, bromo(4-methoxyphenyl)-(9CI), Nov. 16, 1984.
Registration No. 142050-44-0, 4H-1-Benzopyran-4-one, 7-hydroxy-344-methoxy-3-(methoxy-t3)phenyll-(9CI), Jun. 26, 1992.
Registration No. 143358-24-1, 4H-1-Benzopyran-4-one, 2,3-dihydro-7-methoxy-3-(4-methoxyphenyl)-(+)- (9CI), Sep. 9, 1992.
Registration No. 143358-39-8, 4H-1-Benzopyran-4-one, 2,3-dihydro-7-methoxy-3-(4-methoxyphenyl)-(−) (9CI), Sep. 9, 1992.
Registration No. 15236-11-0, 4H-1-Benzopyran-4-one, 2,3-dihydro-7-methoxy-3-(4-methoxyphenyl)-(9CI), Nov. 16, 1984.
Registration No. 16750-63-3, Magnesium, bromo(2-methoxyphenyl)-(9CI), Nov. 16, 1984.
Registration No. 201678-33-3, 4H-1-Benzopyran-4-one, 3-(3,4-dimethoxyphenyl)-2,3- dihydro-7,8-dimethoxy-(9CI), Feb. 22, 1998.
Registration No. 206257-38-7, 4H-1-Benzopyran-4-one, 2, 3-dihydro-3-(4-hydroxyphenyl)-7-methoxy-(9CI), Jun. 3, 1998.
Registration No. 24160-14-3 , 4H-1-Benzopyran-4-one, 3-(3,4-dimethoxyphenyl)-7-hydroxy-(9CI), Nov. 16, 1984.
Registration No. 288267-24-3, 4H-1-Benzopyran-4-one, 7-hydroxy-3-(4-hydroxy-3-methoxyphenyl)-8-methyl-(9CI), Sep. 6, 2000.
Registration No. 304892-19-1, 4H-1-Benzopyran-4-one, 3-(3,4-dihydroxyphenyl)-2,3-dihydro-7-hydroxy-(9CI), Nov. 29, 2000.
Registration No. 36282-40-3, Magnesium, bromo(3-methoxyphenyl)-, Nov. 16, 1984.

(56) References Cited

OTHER PUBLICATIONS

Registration No. 39604-72-3, 4H-1-Benzopyran-4-one, 2,3-dihydro-7methoxy-3-(4-methoxyphenyl)-8-methyl-(9CI), Nov. 16, 1984.
Registration No. 4626-22-6, 4H-1-Benzopyran-4-one, 2,3-dihydro-7-hydroxy-3-(4-methoxyphenyl)-(9CI), Nov. 16, 1984.
Registration No. 67492-31-3, 4H-1-Benzopyran-4-one, 2,3-dihydro-7-hydroxy-3-(3-hydroxy-4-methoxyphenyl)-(9CI), Nov. 16, 1984.
Registration No. 680195-83-9, 4H-1-Benzopyran-4-one, 2,3-dihydro-7,8-dihydroxy-3-(4-hydroxyphenyl)-(9CI), May 6, 2004.
Registration No. 83206-83-1, 4H-1-Benzopyran-4-one, 3-(3,4-dimethoxyphenyl)-2,3-dihydro-7-hydroxy-(9CI), Nov. 16, 1984.
Registration No. 85915-64-6, 2H-1-Benzopyran-7-ol, 4-[5-(3,4-dihydro-7-hydroxy-2-H-1-benzopyran-3 -yl)-4-hydroxy-2-methoxyphenyl]-3 ,4-dihydro-3-(2-hydroxy-4-methoxyphenyl)-, [3S-[3α-4β(R*)]]-(9CI), date unavailable.
Registration No. 85915-66-8, 2H-1-Benzopyran,4-[5-(3,4-dihydro-7-methoxy-2H-1-benzopyran-3-yl)-2,4- dimethoxyphenyl]-3-(2,4-dimethoxyphenyl)-3,4-dihydro-7-methoxy-,[3S-[3α4β(R*)]]-(9CI), date unavailable.
Registration No. 95307-73-6, 4H1-Benzopyran-4-one-2-d, 2,3-dihydro-2-d-7-hydroxy-3-(4-methoxyphenyl)-(9CI), Mar. 16, 1985.
Registration No. 95457-39-9, 4H-1-Benzopyran-4-one-4-14C, 3-(3,4-dimethoxyphenyl)-7-hydroxy-(9CI), Mar. 23, 1985.
Registration No. 95541-42-7, 1,3-Benzenediol, 4-[3,4-dihydro-3-(2-hydroxy-4-methoxyphenyl)-7-methoxy-2H-1-benzopyran-4-yl]-,(3R-trans)-(9CI), date unavailable.
Registration No. 95541-43-8, 2H-Benzopyran,3,4-bis(2,4-dimethoxyphenyl)-3,4-dihydro-7-methoxy-,(3R-trans)-(9CI), date unavailable.
Registration No. 95541-44-9, 1,3,5-Benzenetriol,2-[3,4-dihydro-3-(2-hydroxy-4-methoxyphenyl)-7-methoxy-2H-1-benzopyran-4-yl)-,(3R-trans)-(9CI), date unavailable.
Registration No. 95541-45-0, 1,3,5-Benzenetriol,2,4-bis[3,4-dihydro-3-(2-hydroxy-4-methoxyphenyl)-7- methoxy-2H-1-benzopyran-4-yl]-,[3R-[3α,4β(3(3R*,4S"])-(9CI), date unavailable.
Registration No. 95541-46-1, 2H-1-Benzopyran,3-(2,4-dimethoxyphyenyl)-3,4-dihydro-7-methoxy-4(2,4,6-trimethoxyphenyl)-,(3R-trans)-(9CI), date unavailable.
Registration No. 95541-51-8, 2H-1-Benzopyran-7-ol,3-[3,4-dihydro-3-(2-hydroxy-4-methoxyphenyl)-7- methoxy-2H-1-benzopyran-4-yl]-2-hydroxy-4-methoxyphenyl]- 3,4-dihydro-,[3R-3α,4β(S*)]]-(9CI), date unavailable.
Registration No. 95541-53-0, 2H-1-Benzopyran,4-[5(3,4-dihydro-7-methoxy-2H-1-benzopyran-3-yl)-2,4- dimethoxyphenyl]-3-(2,4-dimethoxyphenyl)-3,4-dihydro-7-methoxy-,[3R-[3α,4β(S*)]]-(9CI), date unavailable.
Registration No. 95541-54-1, 2H-1-Benzopyran-7-ol,3-[-[4-dihydro-4-[4-hydroxy-5-(7-hydroxy-2H-1-benzopyran-3yl)-2-methoxyphenyl]-3-(2-hydroxy-4-methon/phenyl)-(3S-trans)-(9CI), date unavailable.
Registration No. 95541-57-4, 2H-1-Benzopyran,4-[2,4-dimethoxy-5-(7-methoxy-2H-1-benzopyran-3-yl)phenyl]-3-(2,4-dimethoxyphenyl)-3,4-dihydro-7-methoxy-,(3S-trans)-(9CI), date unavailable.
Registration No. 95541-66-5, 2H-1-Benzopyran,4-(2,4-dimethoxyphenyl)-3,4-dihydro-7-methoxy-3-[4-methoxy-2-(methoxymethoxy)phenyl]-,(3R-trans)-(9CI), date unavailable.
Registration No. 95762-78-0, 2H-1-Benzopyran,4,4'-(2,4,6-trimethoxy-1,3-phenylene)bix[3-(2,4- dimethoxyphenyl)-3,4-dihydro-7-methoxy-,[3R[3α,4β(3'R*,4'S*)]]-(9CI), date unavailable.
Scambia, et al., Antiproliferative effect of silybin on gynaecological malignancies;synergism with cisplatin and doxorubicin. Eur J Cancer. May 1996; 32A(5):877-82 (Abstract Only in English).
Scambia, G. Synergistic antiproliferative activity of quercetin and cisplatin on ovarian cancer cell growth. Anti-Cancer Drugs Oct. 1990; 1(1):45-8 (Abstract Only in English).
Sepulveda-Boza, et al., The preparation of new isoflavones, Synthetic Communications. 2001; 3(12):1933-40.
Szlosarek, et al., Tumour necrosis factor a: a potential target for the therapy of solid tumours. The Lancet Oncology. Sep. 2003; 4:565-73.
Tamura, et al., Genistein Enhances the Cisplatin-Induced Inhibition of Cell Growth and Apoptosis in Human Malignant Melanoma Cells. Pigment Cell Res. 2003; 16:470-76 (Abstract Only in English).
Teo, et al., Synthesis of 3-(p-fluorophenyl)-4-arylchrom-3-enes as selective ligands for antiestrogen-binding sites. J Chem Res. Synopses. 1990; 1:4-5 (Abstract Only in English).
Teo, et al., Synthesis of arylchromenes and arylchromans. Bulletin of the Singapore National Institute of Chemistry. 1994; 22:69-74 (Abstract Only in English).
Todorov, et al., Role of a proteolysis-inducing factor(PIF) in a cachexia induced by a human melanoma(G361). Br J Cancer. 1999; 80(11):1734-37.
U.S. Appl. No. 13/891,975 Notice of Allowance mailed Oct. 6, 2014.
U.S. Appl. No. 14/186,940 Office Action mailed Nov. 21, 2014.
Varady, J. The flavonoids of Podocarpus spicatus. I. Structure of podospicatin. Synthesis of podospicatin mono-,di-, and trimethyl ethers. Periodica Polytech. 1963; 7(4):241-58 (Abstract Only in English).
Verma et al., Smooth Conversion of 3,4-Diarylcoumarins and 3,4,5-Triaryl-2(5H)-furanones to 2H-Chromene and 2,5-Dihydrofuran Derivatives with Dimethyl Sulfide-Borane Complex. Synthesis. 1988; 1:68-70.
Voss, C. et al., New isoflavonoids as inhibitors of porcine 5-lipoxygenase. Biochem Pharmacol. 1992; 44(1):157-62 (Abstract Only in English).
Waud, et al., Antitumor drug cross-resistance in vivo in a cisplatin-resistant murine P388 leukemia, Cancer Chemotherapy and Pharmacology. 1991; 27 (6):456-63 (Abstract Only in English).
Weidenborner, et al., Control of storage fungi of the genus Aspergillus on legumes with flavonoids and isoflavonoids. Angewandte Botanik. 1990; 64(1-2):175-90 (Abstract Only in English).
Wolfbeis, et al., The Absorption and Fluorescence of Isoflavones and the Effect of Shift Reagents. Z Naturforsch. Sep. 23, 1984; 39b:238-43.
Zyner, et al., Platinum(II) and palladium(II) N,0-Chelates with substituted flavanone containing ligangs. Acta Pol Pharm. 1999; 56(2): 159-67.
Zyner, et al., Pt(II) and Pt(II) complexes of 3-aminoflavone: In vitro and in vivo evaluation. Pharmazie. 1999; 54(12):945-46.

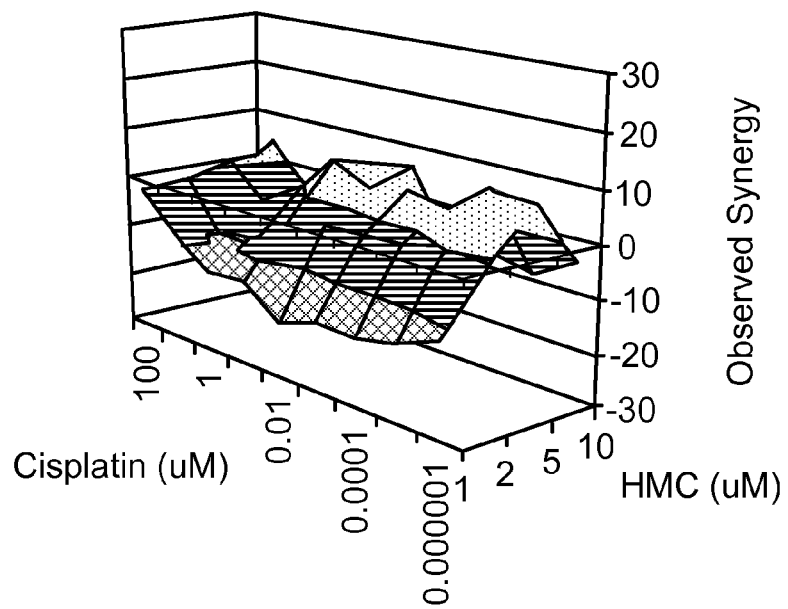
FIG. 10A
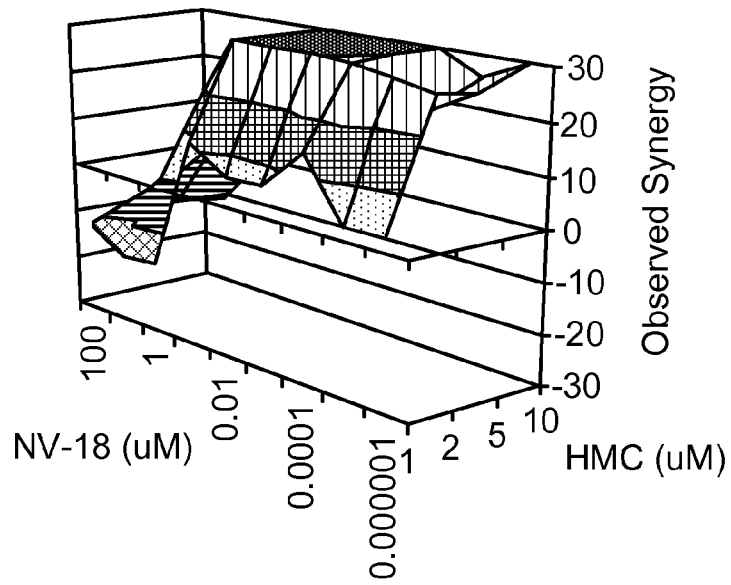
FIG. 10B
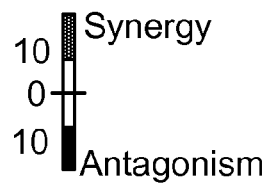
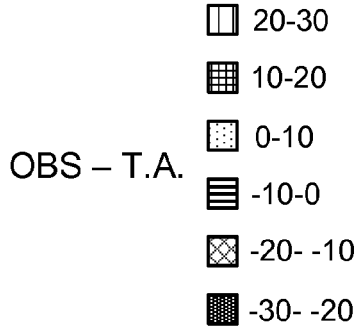

CHROMAN DERIVATIVES, MEDICAMENTS AND USE IN THERAPY

CROSS REFERENCE

This application is a continuation of U.S. application Ser. No. 13/891,975, filed May 10, 2013, now U.S. Pat. No. 8,957,109, issued Feb. 17, 2015, which is a continuation of U.S. application Ser. No. 13/415,697, filed Mar. 8, 2012, now U.S. Pat. No. 8,461,361, issued Jun. 11, 2013, which is a continuation of U.S. application Ser. No. 13/231,794, filed Sep. 13, 2011, now U.S. Pat. No. 8,163,795, issued Apr. 24, 2012, which is a divisional patent application of U.S. application Ser. No. 11/230,505, filed Sep. 21, 2005 entitled "CHROMAN DERIVATIVES, MEDICAMENTS AND USE IN THERAPY", now U.S. Pat. No. 8,080,675, issued Dec. 20, 2011, which claims benefit of U.S. Provisional Application No. 60/611,299, entitled "COMPOUNDS" filed on Sep. 21, 2004; of U.S. Provisional Application No. 60/676,934, entitled "CHROMAN DERIVED COMPOUNDS & FORMULATIONS THEREOF FOR USE IN THERAPY" filed on May 3, 2005; of PCT application No. PCT/AU04/01619, entitled "COMBINATIONAL RADIOTHERAPY AND CHEMOTHERAPY COMPOSITIONS AND METHODS" filed on Nov. 19, 2004; of AU application 2004/906363, entitled "COMPOUNDS" filed Nov. 5, 2004; and of JP application 2004/315009 entitled "COMPOUNDS" filed Oct. 29, 2004; all of which are herein incorporated by reference in their entirety.

FIELD OF THE INVENTION

The present invention relates to certain novel chroman derivatives, compositions containing same, methods for their preparation and uses thereof as therapeutic agents particularly as anti-cancer and chemotherapeutic selective agents.

BACKGROUND OF THE INVENTION

Over 700 different naturally occurring isoflavones are known some of which have biological properties with potential therapeutic benefit.

U.S. Pat. No. 5,726,202 generically discloses certain isoflavan compounds, particularly 3,4-diarylchroman and centchroman for the treatment of benign prostatic hypertrophy.

WO 01/17986 also discloses certain isoflavan compounds.

SUMMARY OF THE INVENTION

Surprisingly, the present inventors have found a novel group of compounds of the general formula (I) which exhibit important therapeutic activities including strong anti-cancer activity, chemotherapeutic selectivity and radiosensitisation of cancers.

Thus according to an aspect of the present invention there is provided a compound of the general formula (I):

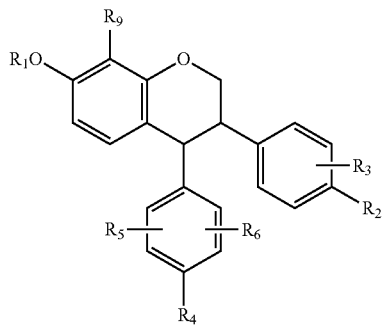

wherein $R_1$ is hydrogen, alkyl, cycloalkyl or $C(O)R_7$, $R_2$ and $R_3$ are independently hydrogen, hydroxy, alkoxy, alkyl, cycloalkyl, halo or $OC(O)R_7$, with the exception that $R_2$ and $R_3$ are not both hydrogen, $R_4$, $R_5$ and $R_6$ are independently hydrogen, hydroxy, alkoxy, alkyl, cycloalkyl, acyl, amino, $C_{1-4}$-alkylamino or di($C_{1-4}$-alkyl)amino, $OC(O)R_7$ or $OR_8$, $R_7$ is hydrogen, alkyl, cycloalkyl, aryl, arylalkyl or amino, and $R_8$ is aryl such as phenyl or arylalkyl such as benzyl, and $R_9$ is hydrogen hydroxy, alkyl, alkoxy, cycloalkyl or halo, or a pharmaceutically acceptable salt or derivative thereof.

In a preferred embodiment of the present invention $R_9$ is hydrogen. Accordingly, in another aspect of the invention there is provided a compound of the formula (I-a):

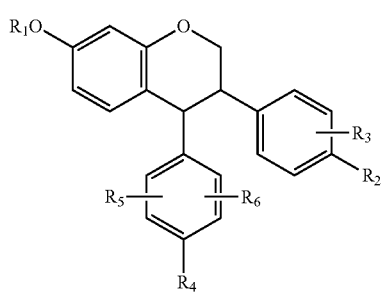

wherein $R_1$ is hydrogen, alkyl, cycloalkyl or $C(O)R_7$, $R_2$ and $R_3$ are independently hydrogen, hydroxy, alkoxy, halo or $OC(O)R_7$, with the exception that $R_2$ and $R_3$ are not both hydrogen, $R_4$, $R_5$ and $R_6$ are independently hydrogen, hydroxy, alkoxy, alkyl, cycloalkyl, acyl, $OC(O)R_7$, amino, and $R_7$ is hydrogen, alkyl, cycloalkyl, aryl, arylalkyl or amino.

According to another aspect of the present invention there is provided a process for the preparation of a compound of formula (I) comprising the step of reacting the keto group of a compound of the formula (II):

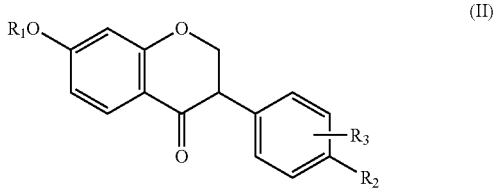

or the analogue thereof including a substituent which corresponds to $R_9$ in compounds of formula (I) wherein
$R_1$, is alkyl or a protecting group such as $Si(R_{10})_3$,
$R_2$ and $R_3$ are independently hydrogen, alkoxy or $OSi(R_{10})_3$, with the exception that $R_2$ and $R_3$ are not both hydrogen, and
$R_{10}$ is independently alkyl or aryl,
with an arylating agent $W^-M^+$,
wherein
$W^-$ is an optionally substituted aryl radical, and
$M^+$ is one or more counter ions, preferably $[MgBr]^+$,
to form the intermediate tertiary alcohol of formula (III):

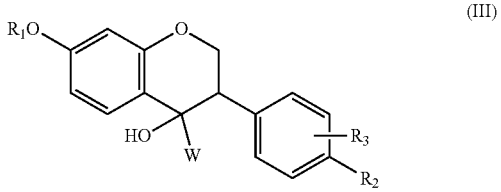

or protected derivative thereof or a salt thereof (or an analogue thereof including a substituent which corresponds to $R_9$ in compounds of formula (I)) and which is dehydrated to form a compound of formula (IV):

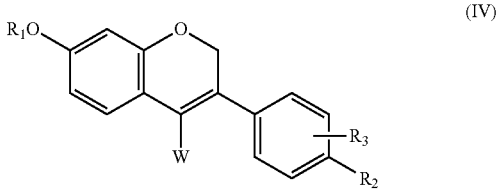

(or an analogue thereof including a substituent which corresponds to $R_9$ in compounds of formula (I)) the double bond of which is subsequently reduced, for example, by hydrogenation and optionally deprotected to form a compound of formula (I).

According to another aspect of the present invention there is provided a compound of the general formula (III), compositions containing same and uses thereof.

In another aspect, there is provided a compound of the general formula (IV), compositions containing same and uses thereof.

Thus, according to another aspect of the present invention there is provided the use of a compound of formula (I) in therapy, particularly chemotherapy and/or as a radiosensitising or chemosensitising agent.

According to another aspect of the present invention there is provided a method for the treatment, prevention or amelioration of a disease or disorder, which comprises administering to a subject one or more compounds of the formula (I) or a pharmaceutically acceptable salt or derivative thereof optionally in association with a carrier and/or excipient.

According to another aspect of the present invention there is provided the use of one or more compounds of formula (I) or a pharmaceutically acceptable salt or derivative thereof in the manufacture of a medicament for the treatment of a disease or disorder.

According to another aspect of the present invention there is provided an agent for the treatment, prophylaxis or amelioration of a disease or disorder which agent comprises one or more compounds of formula (I) or a pharmaceutically acceptable salt or derivative thereof.

According to another aspect of the present invention there is provided a pharmaceutical composition which comprises one or more compounds of formula (I) or a pharmaceutically acceptable salt or derivative thereof in association with one or more pharmaceutical carriers, excipients, auxiliaries and/or diluents.

According to another aspect of the present invention there is provided a drink or food-stuff, which contains one or more compounds of formula (I) or a pharmaceutically acceptable salt or derivative thereof.

These and other aspects of the invention will become evident from the description and claims which follow, together with the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10A and FIG. 10B represent a 3D analysis of HMC-cisplatin synergy cytotoxicity data in the MM200 melanoma cell line. HMC-cisplatin combinations were assessed using a 5-day combination protocol (FIG. 10A), or a 24 hr HMC→anti-cancer sequence (FIG. 10B). For each combination experiment HMC was assessed at 10, 5, 2 and 1 µM. See Table 8 for raw data.

DETAILED DESCRIPTION OF THE INVENTION

Figure 1:
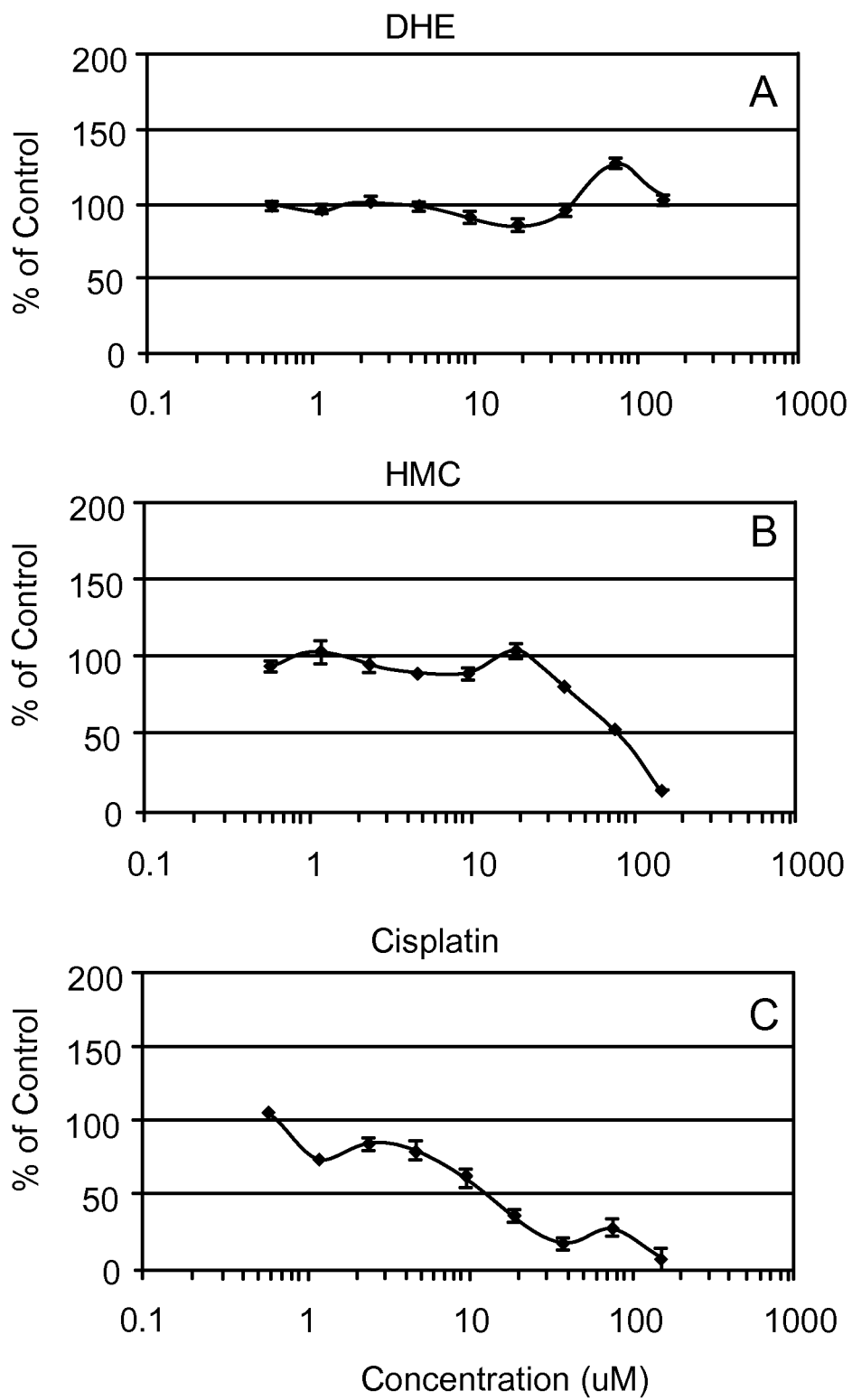
FIG. 1 represents a comparison of dehydroequol (DHE graph A), 3-(4-hydroxyphenyl)-4-(4-methoxyphenyl)chroman-7-ol (HMC compound 1 according to the invention graph B) and cisplatin (graph C) toxicity in neonatal foreskin fibroblasts.

The present inventors have found that a class of isoflavan derivatives of the general formula (I) show surprising and unexpected biological and pharmaceutical properties.

The compounds of formula (I) of the invention are believed to have favourable toxicity profiles with normal cells and good bioavailability. Surprisingly the compounds of the invention exhibit anti-cancer activity, significantly better than or at least comparable to known cancer treatments.

The compounds of formula (I) are cytostatic and cytotoxic against a broad range of cancer cells of human and animal origin. By cancer cells, it is meant cells that display malignant characteristics and which are distinguished from non-cancer cells by unregulated growth and behaviour which usually ultimately is life-threatening unless successfully treated.

The cancer cells that have been found to be responsive to compounds of formula (I) are of epithelial origin (for example, prostate, ovarian, cervical, breast, gall-bladder, pancreatic, colorectal, renal, and non-small lung cancer cells), of mesenchymal origin (for example, melanoma, mesothelioma and sarcoma cancer cells), and of neural origin (for example glioma cancer cells). It is highly unusual and surprising to find a related group of compounds that display such potent cytotoxicity against cancer cells, but with low toxicity against non-cancer cells such as keratinocytes derived from human foreskin. Such cancer cell selectivity is highly unusual and unexpected.

Advantageously the compounds of formula (I) show cytotoxicity against cancer cells that are well recognised for being poorly sensitive to standard anti-cancer drugs. It is highly unusual and unexpected to find such potent activity against cancers, for example, cholangiocarcinoma, pancreatic adenocarcinoma and melanoma.

Advantageously the compounds of formula (I) also unexpectedly display an ability to radio-sensitise cancer cells, by which it is meant that these compounds either lower the amount of gamma-irradiation that is required to kill the cells, or they convert cancer cells from a state of radio-resistance to a radio-sensitive state.

Additionally the compounds of formula (I) are thought to possess chemo-sensitising activity, that is they increase the cytotoxicity of chemotherapeutic agents, especially to cancer cells, and/or convert cancerous cells from a state of chemo-resistance to a chemo-sensitive state.

Compounds of the invention may also provide chemo and/or radio-protective properties for non-cancerous cells. This has significant therapeutic implications because the traumatic side-effects of chemotherapy and radiotherapy are caused by the toxicity of the traditional treatments to non-cancerous cells.

The properties described above offer significant clinical advantages.

The radio and/or chemo-protective properties of the compounds of the invention may be employed to protect healthy individuals from the effects of radiation and/or chemical toxins, or lessen the effects of the same.

Thus, the invention also provides the use of compounds of formula (I) to treat patients with cancer by either reducing the rate of growth of such tumours or by reducing the size of such tumours through therapy with said compounds alone, and/or in combination with each other, and/or in combination with other anti-cancer agents, and/or in combination with radiotherapy.

The use of compounds of the present invention either alone or in combination therapy as described above may reduce the adverse side-effects often experienced by patients when treated with standard anti-cancer treatments. The use of compounds of the invention may mean that lower doses can be employed in such therapy which represents an important advance for cancer sufferers.

Preferably $R_3$ in compounds of formula (I) is in the 3-position.

In another aspect of the invention $R_9$ is $C_{1-4}$-alkyl, such as methyl.

Preferably in compounds of formula (I-a):
$R_1$ is hydrogen, $C_{1-4}$-alkyl or $C(O)R_7$,
$R_2$ and $R_3$ are independently hydrogen, hydroxy, $C_{1-4}$-alkoxy, halo or $OC(O)R_7$, provided that $R_2$ and $R_3$ are not both hydrogen,
$R_4$, $R_5$ and $R_6$ are independently hydrogen, hydroxy, alkoxy, alkyl, cycloalkyl, acyl, $OC(O)R_7$, and
$R_7$ is $C_{1-4}$-alkyl, phenyl or benzyl,
or a pharmaceutically acceptable salt or derivative thereof.

More preferably in compounds of formula (I-a):
$R_1$ is hydrogen, methyl, ethyl, propyl, isopropyl or acetyl,
$R_2$ and $R_3$ are independently hydrogen, hydroxy, methoxy, ethoxy, propoxy, isopropoxy, bromo, chloro, fluoro or acetyloxy, with the exception that $R_2$ and $R_3$ are not both hydrogen,
$R_4$ is hydrogen, hydroxy, methoxy, ethoxy, propoxy, isopropoxy or acetyloxy, and
$R_5$ and $R_6$ are independently hydrogen, hydroxy, methoxy, ethoxy, propoxy, isopropoxy, acetyl, or acetyloxy,
or a pharmaceutically acceptable salt or derivative thereof.

Particular preferred compounds of formula (I-a) have the following substituents where:
$R_1$ is hydrogen, methyl or acetyl,
$R_2$ and $R_3$ are independently hydrogen, hydroxy, methoxy, bromo or acetyloxy, with the exception that $R_2$ and $R_3$ are not both hydrogen,
$R_4$ and $R_6$ are independently hydrogen, hydroxy, methoxy or acetyloxy, and
$R_5$ is hydrogen,
or a pharmaceutically acceptable salt or derivative thereof.

The invention also extends to compounds of formula (I-b):

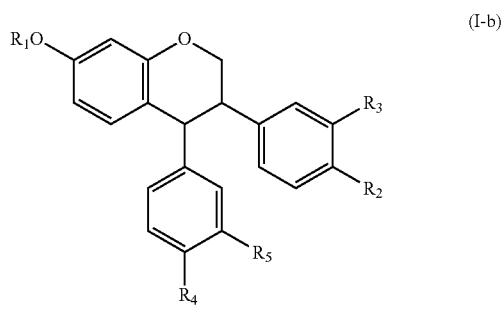

wherein:
$R_1$ represents hydrogen or $C_{1-6}$-alkyl, more preferably hydrogen or methyl, especially hydrogen.
R2 represents hydrogen, hydroxy or $C_{1-6}$-alkoxy such as methoxy, ethoxy, propoxy, more preferably hydroxy or methoxy, especially hydroxy.
$R_3$ represents hydrogen, hydroxy, $C_{1-6}$-alkoxy such as methoxy, ethoxy, propoxy, more preferably hydrogen or methoxy, especially hydrogen, with the proviso that $R_2$ and $R_3$ do not both represent hydrogen,
$R_4$ represents hydrogen, hydroxy, $C_{1-6}$-alkoxy such as methoxy, ethoxy, propoxy, $C_{1-6}$-alkyl such as methyl, ethyl, propyl, isopropyl, especially hydrogen, hydroxy, methoxy or methyl particularly methoxy or hydroxy,
$R_5$ represents hydrogen, $C_{1-6}$-alkoxy, especially hydrogen, methoxy, hydroxy, particularly hydrogen,
or a pharmaceutically acceptable salt or derivative thereof.

Preferred compounds of the invention include those of the general formula (I-c):

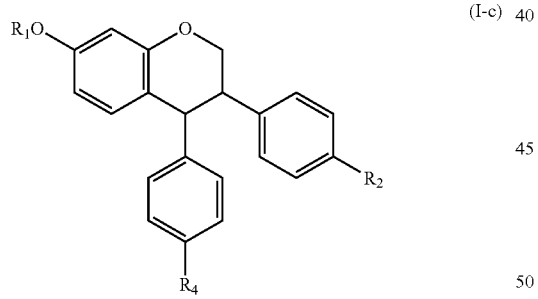

wherein:
$R_1$ is hydrogen or $C_1$-$C_6$ alkyl such as methyl, ethyl, propyl, isopropyl, butyl, isobutyl, secbutyl, tertiary butyl,
$R_2$ is hydroxy or $C_{1-6}$-alkoxy such as methoxy, ethoxy, propoxy, isopropoxy, butoxy, isobutoxy, secbutoxy, tertiary butoxy, and
$R_4$ is hydroxy or $C_{1-6}$-alkoxy such as methoxy, ethoxy, propoxy, isopropoxy, butoxy, isobutoxy, secbutoxy, tertiary butoxy
or a pharmaceutically acceptable salt or a derivative thereof.

More preferably in compounds of formula (I-c) $R_1$ is hydrogen or methyl, especially hydrogen.

More preferably in compounds of formula (I-c) $R_2$ is hydroxy or methoxy, especially hydroxy.

More preferably in compounds of formula (I-c) $R_4$ is hydroxy or methoxy, especially methoxy.

In an alternative aspect the invention provides compounds of formula (I-d):

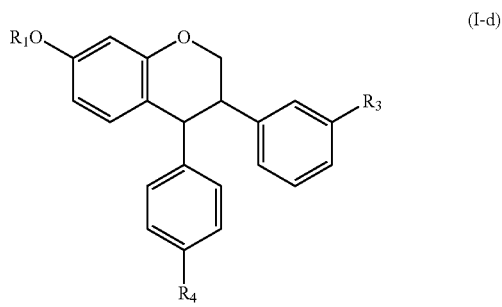

wherein:
$R_1$ is hydrogen, alkyl, cycloalkyl or C(O)$R_7$, and
$R_3$ is hydroxy, alkoxy, alkyl, cycloalkyl, halo or OC(O)$R_7$, with the exception that $R_2$ and $R_3$ are not both hydrogen,
$R_4$ is hydrogen, hydroxy, alkoxy, alkyl, cycloalkyl, acyl, amino, $C_{1-4}$-alkylamino or di($C_{1-4}$-alkyl)amino or OC(O)$R_7$, and
$R_7$ is hydrogen, alkyl, cycloalkyl, aryl, arylalkyl or amino.

In a further alternative aspect the invention provides compounds of formula (I-e):

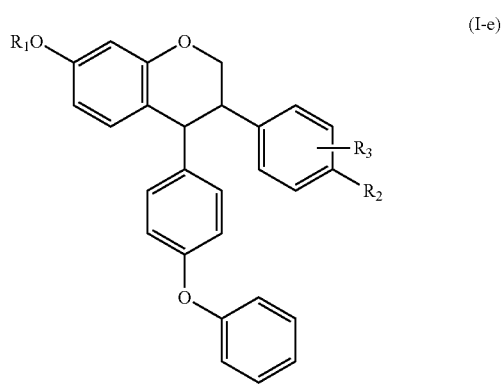

wherein:
$R_1$ is hydrogen, alkyl, cycloalkyl or C(O)$R_7$, and
$R_2$ and $R_3$ are independently hydrogen, hydroxy, alkoxy, alkyl, cycloalkyl, halo or OC(O)$R_7$, with the exception that $R_2$ and $R_3$ are not both hydrogen, Preferably in compounds of formula (I-e) $R_1$ represents hydrogen or methyl, especially hydrogen.

Preferably in compounds of formula (I-e) $R_2$ represents hydroxy or $C_1$-$C_6$ alkoxy such as methoxy.

In compounds of formula (I-e) preferably $R_3$ represents hydrogen, hydroxy or methoxy, especially hydrogen.

In a further alternative aspect the invention provides compounds of formula (I-f):

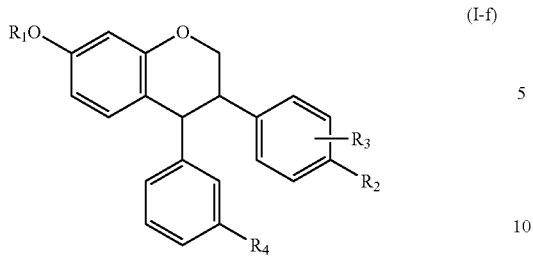

(I-f)

wherein:
$R_1$ is hydrogen, alkyl, cycloalkyl or $C(O)R_7$, and
$R_3$ is hydroxy, alkoxy, alkyl, cycloalkyl, halo or $OC(O)R_7$, with the exception that $R_2$ and $R_3$ are not both hydrogen,
$R_4$ is hydrogen, hydroxy, alkoxy, alkyl, cycloalkyl, acyl, amino, $C_{1-4}$-alkylamino or di($C_{1-4}$-alkyl)amino, $OC(O)R_7$ or $OR_8$, and
$R_7$ is hydrogen, alkyl, cycloalkyl, aryl, arylalkyl or amino, and
$R_8$ is aryl such as phenyl or arylalkyl such as benzyl.

Preferably in compounds of formula (I-f) $R_1$ represents hydrogen or methyl, especially hydrogen.

Preferably in compounds of formula (I-f) $R_2$ represents hydroxy or $C_{1-6}$-alkoxy such as methoxy, especially hydroxy.

Preferably in compounds of formula (I-f) $R_3$ represents hydrogen or $C_{1-6}$-alkoxy such as methoxy, especially hydrogen.

Preferably in compounds of formula (I-f) $R_3$ is in the 3-position.

Preferably in compounds of formula (I-f) $R_{4a}$ represents amino, $C_{1-4}$-alkylamino or di($C_{1-4}$-alkyl)amino, especially amino.

Especially preferred compounds of formula (I) include:
3-(4-hydroxyphenyl)-4-(4-methoxyphenyl)chroman-7-ol (HMC; Cpd. 1);
3-(4-hydroxyphenyl)-4-phenylchroman-7-ol (Cpd. 2);
3-(4-hydroxyphenyl)-4-(3-methoxyphenyl)chroman-7-ol (Cpd. 3);
3-(3,4-dimethoxyphenyl)-4-(4-methoxyphenyl)chroman-7-ol (Cpd. 4);
3-(4-hydroxyphenyl)-4-(4-methylphenyl))chroman-7-ol (Cpd. 5);
3-(4-methoxyphenyl)-4-(4-methoxyphenyl)-7-methoxychroman (Cpd. 6);
3-(4-hydroxyphenyl)-4-(2,6-dimethoxy-4-hydroxyphenyl)chroman-7-ol (Cpd. 7);
3-(4-hydroxyphenyl)-4-(2-hydroxyphenyl)chroman-7-ol (Cpd. 8);
3-(4-hydroxyphenyl)-4-(3-acyl-2-hydroxy-4-methoxyphenyl)chroman-7-ol (Cpd. 9);
3-(3-hydroxyphenyl)-4-(3-methoxyphenyl)chroman-7-ol (Cpd. 10);
3-(4-hydroxyphenyl)-4-(4-hydroxyphenyl)chroman-7-ol (HHC; Cpd. 11);
3-(4-bromophenyl)-4-(4-methoxyphenyl)chroman-7-ol (Cpd. 12);
3-(4-hydroxyphenyl)-4-(3-methoxyphenyl)chroman-7-ol (Cpd. 13);
3-(4-hydroxyphenyl)-4-(3-aminophenyl)chroman-7-ol (Cpd. 14);
3-(4-hydroxyphenyl)-4-(4-phenoxyphenyl)chroman-7-ol (Cpd. 15);
3-(3,4-dimethoxyphenyl)-4-(4-methoxyphenyl)-8-methylchroman-7-ol (Cpd. 16).

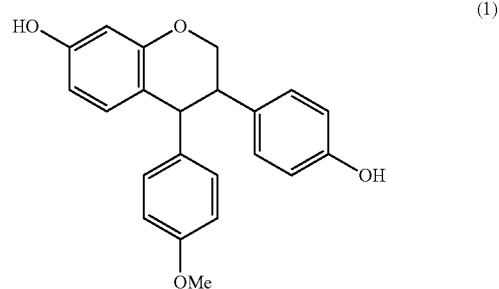

(1)

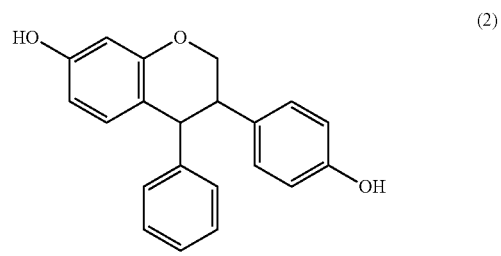

(2)

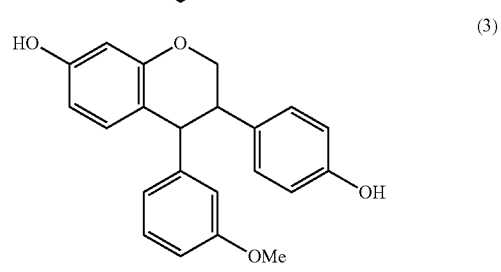

(3)

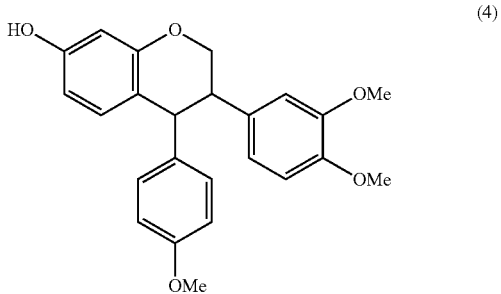

(4)

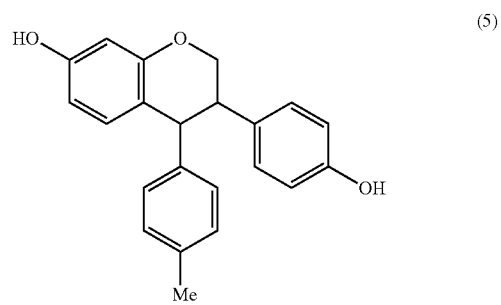

(5)

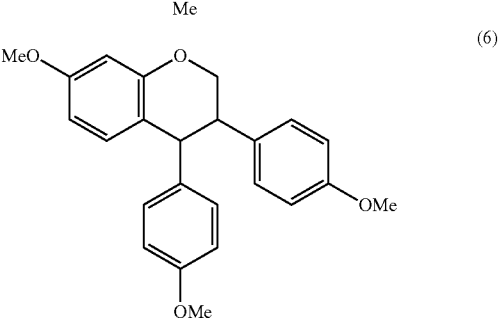

(6)

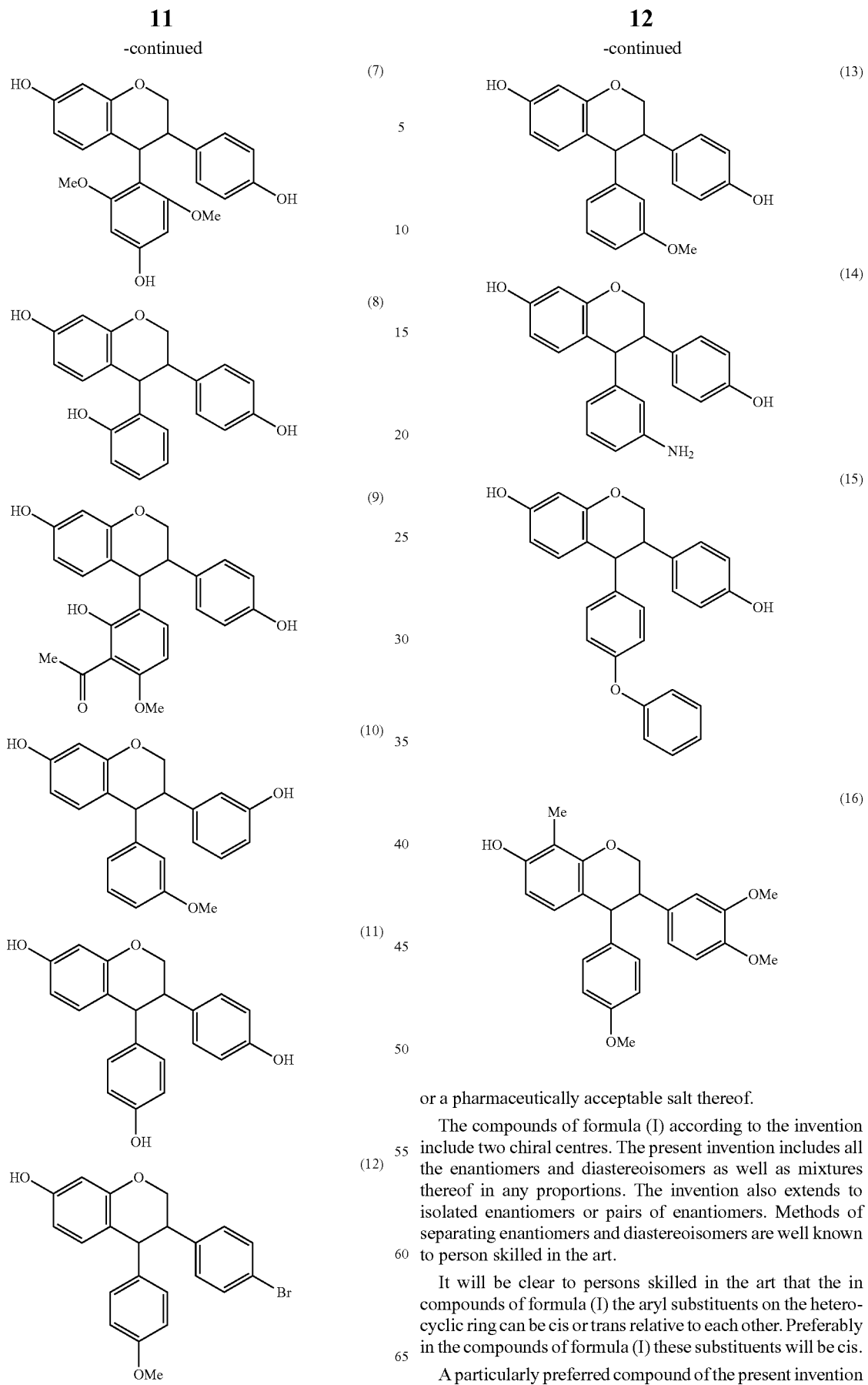

or a pharmaceutically acceptable salt thereof.

The compounds of formula (I) according to the invention include two chiral centres. The present invention includes all the enantiomers and diastereoisomers as well as mixtures thereof in any proportions. The invention also extends to isolated enantiomers or pairs of enantiomers. Methods of separating enantiomers and diastereoisomers are well known to person skilled in the art.

It will be clear to persons skilled in the art that the in compounds of formula (I) the aryl substituents on the heterocyclic ring can be cis or trans relative to each other. Preferably in the compounds of formula (I) these substituents will be cis.

A particularly preferred compound of the present invention is the cis-isomer of compound No. (1), HMC:

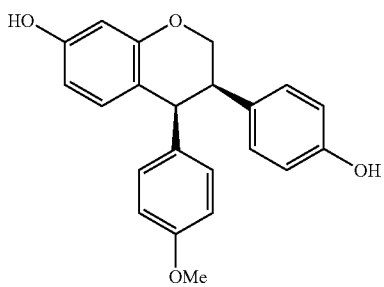 [SMILES: COc1ccc([C@H]2c3ccc(O)cc3OC[C@H]2c2ccc(O)cc2)cc1]

or a pharmaceutically acceptable salt thereof.

Likewise, particularly preferred compounds are compound Nos. (2) to (16) in the cis-conformation.

The compounds of formulae (III) and (IV) are intermediates as set out herein. Each corresponding isoflavan-4-ol and isoflavan-3-ene intermediate of compound Nos. (1) to (16) are also preferred compounds of the present invention.

W in compounds of formula (III) and (IV) may, for example, represent the following radicals:

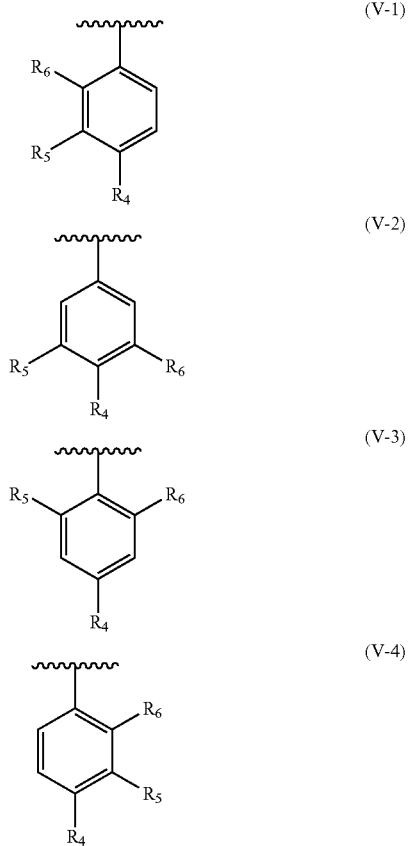

or a protected derivative thereof wherein $R_4$, $R_5$ and $R_6$ are as defined above for compounds of formula (I).

The term "isoflavone" as used herein is to be taken broadly to include as isoflavones, isoflavenes, isoflavans, isoflavanones, isoflavanols and the like.

The term "alkyl" is taken to include straight chain and branched chain saturated alkyl groups of 1 to 6 carbon atoms, such as methyl, ethyl, propyl, isopropyl, butyl, isobutyl, secbutyl, tertiary butyl, pentyl and the like. The alkyl group more preferably contains preferably from 1 to 4 carbon atoms, especially methyl, ethyl, propyl or isopropyl.

Cycloalkyl includes $C_{3-6}$ cycloalkyl such as cyclopropyl, cyclobutyl, cyclopentyl and cyclohexyl.

The alkyl group or cycloalkyl group may optionally be substituted by one or more of fluorine, chlorine, bromine, iodine, carboxyl, $C_1$-$C_4$-alkoxycarbonyl, $C_1$-$C_4$-alkcylamino-carbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cycloalkyl or phenyl.

Preferably the alkyl group does not bear any substituents.

The term "aryl" is taken to include phenyl, benzyl, biphenyl and naphthyl and may be optionally substituted by one or more $C_1$-$C_4$-alkyl, hydroxy, $C_1$-$C_4$-alkoxy, carbonyl, $C_1$-$C_4$-alkoxycarbonyl, $C_1$-$C_4$-alkylcarbonyloxy, nitro or halo.

The term "halo" is taken to include fluoro, chloro, bromo and iodo, preferably fluoro and chloro, more preferably fluor. Reference to for example "haloalkyl" will include monohalogenated, dihalogenated and up to perhalogenated alkyl groups. Preferred haloalkyl groups are trifluommethyl and pentafluoroethyl.

The compounds of the invention include all salts, such as acid addition salts, anionic salts and zwitterionic salts, and in particular include pharmaceutically acceptable salts as would be known to those skilled in the art. The term "pharmaceutically acceptable salt" refers to an organic or inorganic moiety that carries a charge and that can be administered in association with a pharmaceutical agent, for example, as a counter-cation or counter-anion in a salt. Pharmaceutically acceptable cations are known to those of skilled in the art, and include but are not limited to sodium, potassium, calcium, zinc and quaternary amine. Pharmaceutically acceptable anions are known to those of skill in the art, and include but are not limited to chloride, acetate, tosylate, citrate, bicarbonate and carbonate.

Pharmaceutically acceptable salts include those formed from: acetic, ascorbic, aspartic, benzoic, benzenesulphonic, citric, cinnamic, ethanesulphonic, fumaric, glutamic, glutaric, gluconic, hydrochloric, hydrobromic, lactic, maleic, malic, methanesulphonic, naphthoic, hydroxynaphthoic, naphthalenesulphonic, naphthalenedisulphonic, naphthaleneacrylic, oleic, oxalic, oxaloacetic, phosphoric, pyruvic, p-toluenesulphonic, tartaric, trifluoroacetic, triphenylacetic, tricarballylic, salicylic, sulphuric, sulphamic, sulphanilic and succinic acid.

The term "pharmaceutically acceptable derivative" or "prodrug" refers to a derivative of the active compound that upon administration to the recipient is capable of providing directly or indirectly, the parent compound or metabolite, or that exhibits activity itself and includes for example phosphate derivatives and sulphonate derivatives. Thus, derivatives include solvates, pharmaceutically active esters, prodrugs or the like. This also includes derivatives with physiologically cleavable leaving groups that can be cleaved in vivo to provide the compounds of the invention or their active moiety. The leaving groups may include acyl, phosphate, sulfate, sulfonate, and preferably are mono-, di- and per-acyl oxy-substituted compounds, where one or more of the pendant hydroxy groups are protected by an acyl group, preferably an acetyl group. Typically acyloxy substituted compounds of the invention are readily cleavable to the corresponding hydroxy substituted compounds.

Chemical functional group protection, deprotection, synthons and other techniques known to those skilled in the art may be used where appropriate to aid in the synthesis of the compounds of the present invention, and their starting materials.

The protection of functional groups on the compounds and derivatives of the present invention can be carried out by well established methods in the art, for example as described in T. W. Greene, *Protective Groups in Organic Synthesis*, John Wiley & Sons, New York, 1981.

Hydroxyl protecting groups include but are not limited to carboxylic acid esters, eg acetate esters, aryl esters such as benzoate, acetals/ketals such as acetonide and benzylidene, ethers such as o-benzyl and p-methoxy benzyl ether, tetrahydropyranyl ether and silyl ethers such as t-butyldimethyl silyl ether.

Protecting groups can be removed by, for example, acid or base catalysed hydrolysis or reduction, for example, hydrogenation. Silyl ethers may require hydrogen fluoride or tetrabutylammonium fluoride to be cleaved.

It will be clear to persons skilled in the art of medicinal chemistry that compounds of formula (I) may be converted into other compounds of formula (I), for example, where a compound of formula (I) bears one or more hydroxyl substituents then one or more of these substituents can be converted in to a halo substituent such as bromo, chloro or iodo by treating the alcohol with a halogenating agent. Halogenating agents include compounds like NBS, hydrobromic acid, chlorine gas etc. It may be necessary during processes such as halogenation to use protecting groups to protect other functionality in the molecule.

Phenolic type hydroxyls may not be readily convertible to the corresponding halogen compound by treatment with a halogenating agent. However, the desired halogen compound may be prepared by, for example, treating an appropriate aryl amine starting material with $NaNO_2$ in the presence of HCl under reduced temperature conditions such as 0° C., to form the corresponding azide salt. Subsequent treatment with CuCl, CuBr, KI or $HBF_4$ may be used to convert the azide into the required halo-compound.

A general process for preparing compounds of formula (I) comprises the step of treating a compound of formula (IV):

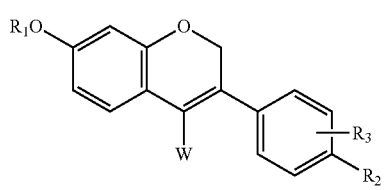

(IV)

wherein $R_1$, $R_2$, $R_3$ and W are as defined above in relation to compounds of formula (II) with a reducing agent to provide a compounds of formula (I) or a protected derivative thereof.

Reducing agents are well known to persons skilled in the art and can include hydride sources like borohydrides and alkali metal borohydrides, but would include hydrogen in catalytic hydrogenation where a suitable catalyst such as palladium on carbon may be used. Other suitable hydride sources include sodium triacetoxyborohydride tetrabutyl ammonium triacetoxyborohydride and sodium cyanoborohydride.

Preferably the double bond in compounds of formula (IV) is reduced by hydrogenation.

Compounds of formula (IV) are prepared by dehydrating a compound of formula (III):

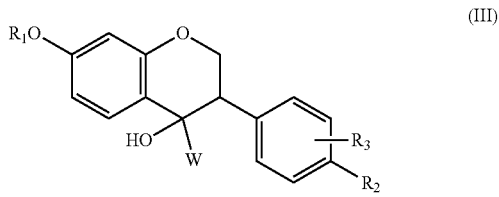

(III)

wherein $R_1$, $R_2$, $R_3$ and W are as defined above, in relation to compounds of formula (II) or a protected derivative thereof.

Dehydration can, for example, be catalysed by acid, by base or facilitated by conversion of the tertiary alcohol into a better leaving group as would be known to those skilled in the art.

Preferably compounds of formula (III) are dehydrated, for example, by treatment with para-toluene sulphonic acid.

Compounds of formula (III) may be prepared by treating compounds of formula (II):

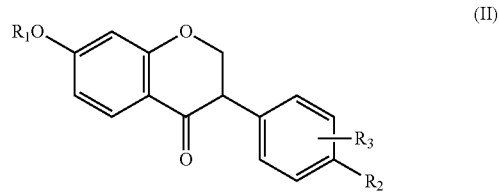

(II)

wherein $R_1$, $R_2$, $R_3$ are as defined above for compounds of formula (II) or a protected derivative thereof with an arylating agent, for example, a compound of formula $W^-M^+$ wherein $W^-$ is an optionally substituted aryl radical and $M^+$ is one or more counter ions, preferably $[MgBr]^+$.

The arylating agent $W^-M^+$ may be prepared by Grignard chemistry where the haloaryl compound (V):

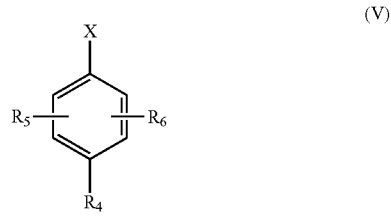

(V)

or a protected derivative thereof wherein $R_4$, $R_5$ and $R_4$ are independently hydrogen, alkoxy, alkyl, acyl, $OC(O)R_7$, a protected hydroxy such as $OSi(R_{10})_3$ or protected amino such as trimethylsilylamino phenyl halide, and $R_{10}$ is independently alkyl or aryl, and X is halo, preferably bromo, is reacted with a metal such as magnesium to form the arylating agent.

Preferably the haloaryl compound (V) is selected from:

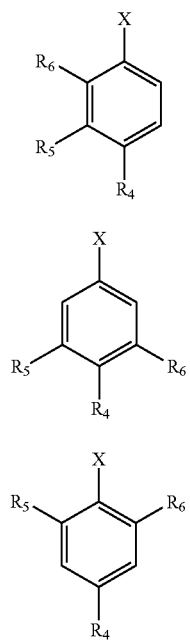

wherein $R_4$, $R_5$, $R_6$ and X are as defined above for compounds of formula (V).

Reaction of the arylating agent with the ketone of formula (II) provides access to the corresponding isoflavan-4-ols (III), isoflav-3-enes (IV) and isoflavans (I) of the present invention.

Alternatively compounds of formula (III) may be prepared by reacting compounds of formula (II) with a compound analogous to compounds of formula (V) wherein X represents any appropriate leaving group L which is lost in the formation of the product by nucleophilic addition of the aryl moiety to a ketone by reactions well known by those skilled in the art.

Preferably any free alcohols, esters or other such reactive groups in the keto compounds of formula (II) will be protected, for example, as t-butyldimethylsilyl ethers during the nucleophilic addition reaction.

Compounds of formula (II) can be prepared by reducing the eneone double bond in compounds of formula (VI):

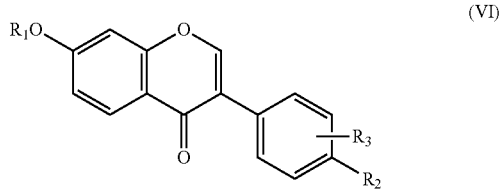

or a protected derivative thereof, wherein $R_1$, $R_2$ and $R_3$ are as defined above, for compounds of formula (II).

Suitable reducing agents are described above. Preferably reduction of the carbon-carbon double bond can be effected, for example, by hydrogenation.

Access to compounds of general formula (VI) is available by general synthetic methods as set out in Scheme 1 below and as described in published International application No. WO01/17986, the disclosure of which is incorporated herein by reference. A typical synthesis is depicted in Scheme I.

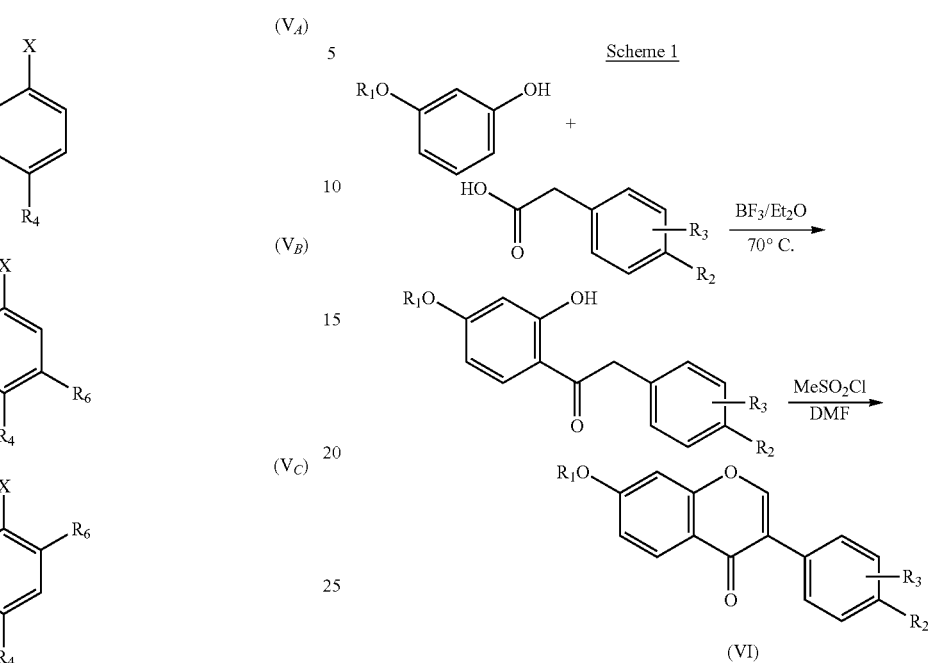

Access to the variatious 3-phenyl substituted chromans is available by varying the substitution pattern on the phenylacetic acid derived group.

Access to the 4-phenyl substituted chromans is available by varying the substitution pattern of the arylating agent (V).

Analogues of compounds employed in the processes may be used which include a substituent which corresponds to $R_9$ as defined for compounds of formula (I).

As used herein, the terms "treatment", "prophylaxis" or "prevention", "amelioration" and the like are to be considered in their broadest context. In particular, the term "treatment" does not necessarily imply that an animal is treated until total recovery. Accordingly, "treatment" includes amelioration of the symptoms or severity of a particular condition or preventing or otherwise reducing the risk of developing a particular condition.

The amount of one or more compounds of formula (I) which is required in a therapeutic treatment according to the invention will depend upon a number of factors, which include the specific application, the nature of the particular compound used, the condition being treated, the mode of administration and the condition of the patient.

Compounds of formula (I) may be administered in a manner and amount as is conventionally practised. See, for example, Goodman and Gilman, "The pharmacological basis of therapeutics", 7th Edition, (1985). The specific dosage utilised will depend upon the condition being treated, the state of the subject, the route of administration and other well known factors as indicated above. In general, a daily dose per patient may be in the range of 0.1 mg to 5 g; typically from 0.5 mg to 1 g; preferably from 50 mg to 200 mg. The length of dosing may range from a single dose given once every day or two, to twice or thrice daily doses given over the course of from a week to many months to many years as required, depending on the severity of the condition to be treated or alleviated.

It will be further understood that for any particular subject, specific dosage regimens should be adjust over time according to the individual need and the professional judgment of the person administering or supervising the administration of the compositions.

Relatively short-term treatments with the active compounds can be used to cause stabilisation or shrinkage or remission of cancers. Longer-term treatments can be employed to prevent the development of cancers in high-risk patients.

The production of pharmaceutical compositions for the treatment of the therapeutic indications herein described are typically prepared by admixture of the compounds of the invention (for convenience hereafter referred to as the "active compounds") with one or more pharmaceutically or veterinary acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain up to 100% by weight of the active compound, preferably from 0.5% to 59% by weight of the active compound.

One or more active compounds may be incorporated in the formulations of the invention, which may be prepared by any of the well known techniques of pharmacy consisting essentially of admixing the components, optionally including one or more accessory ingredients. The preferred concentration of active compound in the drug composition will depend on absorption, distribution, inactivation, and excretion rates of the drug as well as other factors known to those of skill in the art.

The formulations of the invention include those suitable for oral, rectal, ocular, buccal (for example, sublingual), parenteral (for example, subcutaneous, intramuscular, intradermal, or intravenous), transdermal administration including mucosal administration via the nose, mouth, vagina or rectum, and as inhalants, although the most suitable route in any given case will depend on the nature and severity of the condition being treated and on the nature of the particular active compound which is being used.

Formulation suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more other ingredients.

Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatine and glycerin or sucrose and acacia.

Formulations suitable for ocular administration include liquids, gels and creams comprising the active compound in an ocularly acceptable carrier or diluent.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound and can be administered at a rate of 0.1 ml/minute/kg.

Formulations for infusion, for example, may be prepared employing saline as the carrier and a solubilising agent such as α-cyclodextrin or derivative thereof. Suitable cyclodextrins include α-cyclodextrin, β-cyclodextrin, γ-cyclodextrin, dimethyl-β-cyclodextrin, 2-hydroxyethyl-β-cyclodextrin, 2-hydroxypropyl-cyclodextrin, 3-hydroxypropyl-β-cyclodextrin and tri-methyl-β-cyclodextrin. More preferably the cyclodextrin is hydroxypropyl-β-cyclodextrin. Suitable derivatives of cyclodextrins include Captisol® a sulfobutyl ether derivative of cyclodextrin and analogues thereof as described in U.S. Pat. No. 5,134,127.

Formulations suitable for rectal administration are preferably presented as unit dose suppositories. Formulations suitable for vaginal administration are preferably presented as unit dose pessaries. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers which may be used include Vasoline, lanoline, polyethylene glycols, alcohols, and combination of two or more thereof. The active compound is generally present at a concentration of from 0.1% to 5% w/w, more particularly from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound. See for example Brown, L., et al. (1998).

Formulations suitable for transdermal administration may also be delivered by iontophoresis (see, for example, Panchagnula R, et al., 2000) and typically take the form of an optionally buffered aqueous solution of the active compound: Suitable formulations comprise citrate or Bis/Tris buffer (pH 6) or ethanol/water and contain from 0.1 M to 0.2 M active ingredient.

Formulations suitable for inhalation may be delivered as a spray composition in the form of a solution, suspension or emulsion. The inhalation spray composition may further comprise a pharmaceutically acceptable propellant such as carbon dioxide or nitrous oxide or a hydrogen containing fluorocarbon such as 1,1,1,2-tetrafluoroethane, 1,1,1,2,3,3,3-heptafluoro-n-propane or mixtures thereof.

The active compounds may be provided in the form of food stuffs, such as being added to, admixed into, coated, combined or otherwise added to a food stuff. The term food stuff is used in its widest possible sense and includes liquid formulations such as drinks including dairy products and other foods, such as health bars, desserts, etc. Food formulations containing compounds of the invention can be readily prepared according to standard practices.

Therapeutic methods, uses and compositions may be for administration to humans or other animals, including mammals such as companion and domestic animals (such as dogs and cats) and livestock animals (such as cattle, sheep, pigs and goats), birds (such as chickens, turkeys, ducks), marine animals including those in the aquaculture setting (such as fish, crustaceans and shell fish) and the like.

The active compound or pharmaceutically acceptable derivatives prodrugs or salts thereof can also be co-administered with other active materials that do not impair the desired action, or with materials that supplement the desired action, such as antibiotics, antifungals, anti-inflammatories, or antiviral compounds. The active agent can comprise two or more isoflavones or derivatives thereof in combination or synergistic mixture. The active compounds can also be administered with lipid lowering agents such as probucol and nicotinic acid; platelet aggregation inhibitors such as aspirin; anti-thrombotic agents such as coumadin; calcium channel blockers such as verapamil, diltiazem, and nifedipine; angiotensin converting enzyme (ACE) inhibitors such as captopril and enalapril, and β-blockers such as propanolol, terbutalol, and labetalol. The compounds can also be administered in combination with nonsteriodal anti-inflammatories such as ibuprofen, indomethacin, aspirin, fenoprofen, mefenamic acid, flufenamic acid and sulindac. The compounds can also be administered with corticosteroids or an anti-emetic such as Zofrane®.

Compounds of formula (I) seem to be particularly suitable for co-administration with one or more anti-cancer drugs such as cisplatin, dehydroequol (DHE), taxol (paclitaxel), gemcitabine, doxorubicin, topotecan and/or camptothecin, especially cisplatin, dehydroequol (DHE), taxol. This may result in improved effects in the treatment, for example in the form of synergistic effects, in comparison to when only one of the medicaments is employed. Particularly the compounds of the presently claimed invention, especially HMC (ie compound 1) seem to be chemosensitisers and increase the cytotoxicity of the one or more anticancer drug co-administered therewith. This seems to be the case even though said anti-cancer drugs work through a variety of different mechanisms, for example cisplatin is thought to work by interacting with nuclear DNA, taxol is thought to work by blocking cells in the G2/M phase of the cell cycle and prevent them forming normal mitotic apparatus, gemcitabine is thought to work by incorporating itself into the DNA of the cell, ultimately preventing mitosis, doxorubicin is thought to be a topoisomerase II inhibitor thereby preventing DNA replication and transcription and topotecan is thought to be a topoisomerase I inhibitor.

Interestingly, in some situations this increased cytotoxicity to cancerous cells is not associated with a corresponding increase in toxicity to non-cancerous cells.

Whilst this observation has important implications for the treatment of many cancers, it is especially important to the treatment of cancers such as melanoma, which are extremely difficult to treat.

The co-administration may be simultaneous or sequential. Simultaneous administration may be effected by the compounds being in the same unit dose, or in individual and discrete unit doses administered at the same or similar time. Sequential administration may be in any order as required and typically will require an ongoing physiological effect of the first or initial active agent to be current when the second of later active agent is administered, especially where a cumulative or synergistic effect is desired.

The invention also extends to a pack comprising the combination therapy.

Compounds for use in the preferred synthetic methods of the present invention may be derived from any number of sources readily identifiable to a person skilled in the art. For example, daidzein is readily available or can be synthesised by standard methods known in the art. Suitable methods may be found in, for example, published international patent applications WO 98/08503 and WO 00/49009, and references cited therein, which are incorporated herein in their entirety by reference.

Compounds of the general formulae (II), (III) and (IV) described above are intermediates in the production of the active isoflavan compounds of formula (I). These intermediates also represent further aspects of the present invention.

Whilst not wishing to be bound by theory the compounds of the present invention are thought to regulate a wide variety of signal transduction processes within animal cells and that these signal transduction processes are involved in a wide range of functions that are vital to the survival and function of all animal cells. Therefore, these compounds have broad-ranging and important health benefits in animals including humans, and in particular have the potential to prevent and treat important and common human diseases, disorders and functions, which represents a substantial unexpected benefit.

Thus it seems that the compounds of the present invention have activity as TNFα inhibitors. It is hypothesised that TNFα is part of a tightly regulated cytokine network, activating multiple signal transduction pathways and inducing or suppressing a wide variety of genes. TNFα can provide a survival signal for cancer cells and hence it has been referred to as a tumour promoting factor. As a central mediator of inflammation, TNFα provides a molecular link between chronic inflammatory stimuli and the subsequent development of malignant disease. Consequently its inhibition by the compounds of the invention may provide one mechanism by which they exert anti-cancer and/or anti-inflammatory activity. Alternatively, these compounds may be used as chemo-preventative agents.

The particular benefits of this invention lie in (a) the large range of signal transduction processes targeted by the compounds, (b) the fact that regulation of these various processes includes both up-regulation of some processes and down-regulation of others, and (c) that such a broad and varied effect on signal transduction processes also is accompanied by an independent effect on a range of important enzymes that are fundamental to metabolism and steroidogenesis.

The isoflavan compounds of the present invention exhibit good in vitro toxicity profiles against normal cells. The isoflavans have broad activity, markedly better than or at least comparable with dehydroequol. The isoflavans are highly active against cancer cells representative of leukaemia, glioma, prostate, ovarian, breast and lung cancer. The isoflavan compounds show potent activity against melanoma and cholangiocarcinoma (gall bladder cancer) cell lines. Good activity was observed against colorectal cancer cells.

Radio-sensitisation in vivo may be tested for example employing human epidermoid vulval carcinoma A431 tumours established on the upper leg and subjected to several doses of local radiation (to the tumour bearing leg only). A radiation treatment regimen of 2.5 Gy/day for 4 days will delay tumour growth, and the effect of the radiation dose in combination with the test compound could be assessed by monitoring tumour growth delay. Tumour growth delay of ~6 days can be expected using radiation alone. Tumour growth delay using orally dosed test compound can be determined separately. Evidence of test compound mediated radio-sensitisation of A431 tumours is then determined by measuring tumour growth delay using a regimen of orally dosed test compound pre-treated animals followed by the standard radiation therapy regimen described above. A mean growth delay of up to 30 days using the combination treatment compared to up to 10 days using either radiation or test compound monotherapy regimens is evidence of the radio-sensitisation properties of the compounds of the invention.

Radio-sensitisation in vitro may be tested, for example, employing clonogenic assays using human the human epidermoid vulva carcinoma A431 cell line to measure response to radiation alone or in combination with test compounds. A drug dose causing 10% toxicity to the cells may be used in combination with graded doses of radiation. The appropriate dose of compound would be determined by clonogenic assay. Evidence of test compound mediated radio-sensitisation is shown by, for example, a >20% toxicity to cells using chemoradiation therapy compared to 10% toxicity using the corresponding monotherapy regimens.

The compounds of the invention are useful in the treatment, prevention or amelioration of diseases associated with aberrant cell survival, aberrant cell proliferation, abnormal cellular migration, abnormal angiogenesis, abnormal estrogen/androgen balance, dysfunctional or abnormal steroid genesis, degeneration including degenerative changes within blood vessel walls, inflammation, and immunological imbalance.

The invention is further illustrated by the following non-limiting Examples and accompanying drawings.

EXAMPLES

In the Examples and accompanying drawings which follow the abbreviation "DHE" is used for dehydroequol, "HMC" is used for compound No. 1, being 3-(4-hydroxyphenyl)-4-(4-methoxyphenyl)-chroman-7-ol and "HHC" is used for compound No. 11, being 3-(4-hydroxyphenyl)-4-(4-hydroxyphenyl)-chroman-7-ol.

1.0. Synthesis

Example 1

4',7-Diacetoxydatdzein

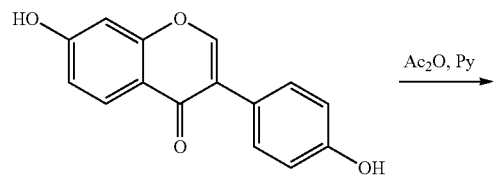

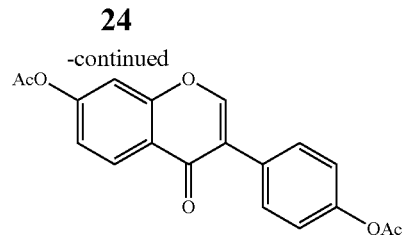

A mixture of daidzein (2.0 g), acetic anhydride (10 ml) and pyridine (2 ml) was heated at 105-110 C for 1 h. After cooling the mixture to room temperature, it was stirred for a further 30 min during which time the diacetate crystallised from solution. The product was filtered, washed thoroughly with water and recrystallised from methanol to yield 4',7-diacetoxydaidzein as colourless prisms (2.4 g, 90%).

Example 2

7-Acetoxy-3-(4-acetoxyphenyl)chroman-4-one

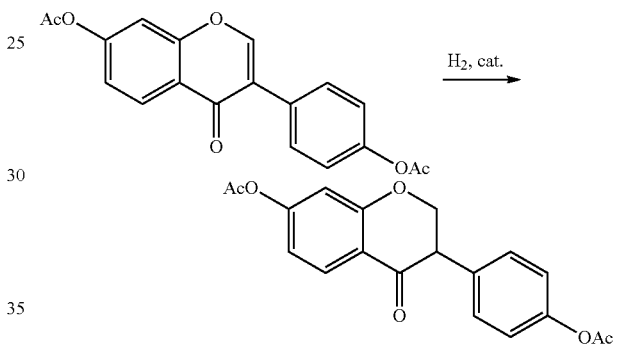

Palladium-on-charcoal (5%, 0.02 g) was added to a solution of 4',7-diacetoxydaidzein (0.50 g, 1.5 mmol) in ethyl acetate (80 ml) and the mixture was stirred at room temperature under a hydrogen atmosphere for 72 h. The catalyst was removed by filtration through Celite and the resulting filtrate was evaporated in vacuo. The residue was recrystallised from ethanol to yield 7-acetoxy-3-(4-acetoxyphenyl)chroman-4-one (0.40 g, 80%) as colourless plates.

Example 3

7-Hydroxy-3-(4-hydroxyphenyl)chroman-4-one

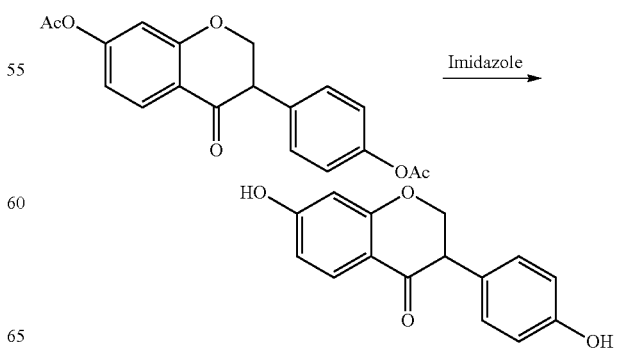

Imidazole (0.63 g) was added to a suspension of 4',7-diacetoxydihydrodaidzein (0.26 g, 0.08 mmol) in absolute ethanol (5.0 ml) and the mixture was refluxed for 45 min under argon. The solution was concentrated under reduced pressure and distilled water (10 ml) was added to the residue. The mixture was left overnight under refrigeration and the resulting precipitate was filtered. The crude product was recrystallised from ethyl acetate/dichloromethane to yield 7-hydroxy-3-(4-hydroxyphenyl)chroman-4-one (0.14 g, 71%) as a white powder.

Example 4

7-(tert-Butyldimethlysilyloxy)-3-(4-(tert-butyldimethlysilyloxy)phenyl)chroman-4-one

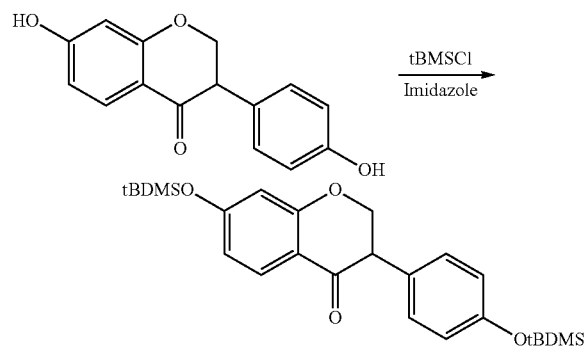

7-Hydroxy-3-(4-hydroxyphenyl)chroman-4-one 42 g, imidazole 130 g, tert-butyldimethylsilyl chloride 127 g, and N,N-dimethylformamide (500 ml) were combined in a 2 L round bottom flask and stirred under nitrogen at room temperature for 16 hours. The reaction was quenched with the addition of chilled $H_2O$ (200 ml) with the reaction mix cooled in an ice bath. The resultant white solid was filtered and rinsed with water. Recrystallisation from ethanol afforded the product as white fluffy crystals (35.7 g).

Example 5

7-(tert-Butyldimethylsilyloxy)-3-(4-(tert-butyldimethylsilyloxy)phenyl)-4-(4-methoxyphenyl)chroman-4-ol

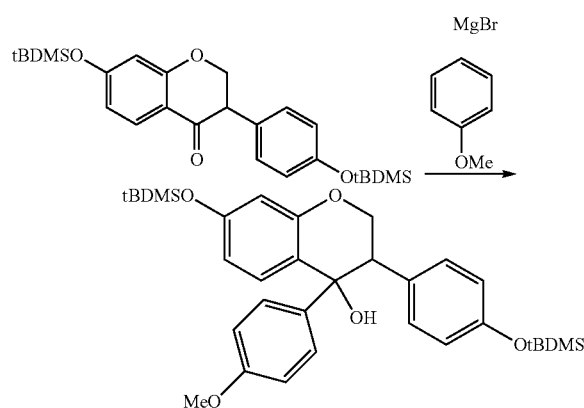

7-(tert-Butyldimethylsilyloxy)-3-(4-(tert-butyldimethylsilyloxy)phenyl)-4-(4-methoxypenyl)chroman-4-ol 25 g was weighed in a 2-neck round bottom flask, and flushed under nitrogen. Anhydrous THF 80 ml was added to the reaction vessel to give a clear slightly yellow solution. A condenser was attached and the reaction vessel placed in an ice bath. Commercial 4-methoxyphenylmagnesium bromide (0.5M solution in THF) 225 ml was added to the reaction mix dropwise over 10 minutes. The reaction was quenched by the dropwise addition of wet ether (50:50 $H_2O$:diethyl ether) while still under nitrogen, with a white precipitate forming as increasing amounts of $H_2O$ was added. A further amount of $H_2O$ was added to the reaction mix before extraction with diethyl ether.

The organic layers were combined and washed with water, brine, dried over anhydrous $MgSO_4$ and solvent removed on rotovap to give clear yellow oil which solidified overnight to give an off-white solid. The crude product was used in the next step without purification.

Example 6

3-(4-Hydroxyphenyl)-4-(4-methoxyphenyl)-2H-chromen-7-ol

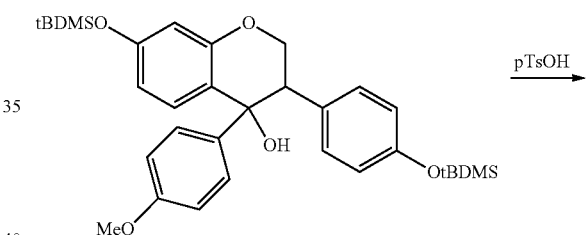

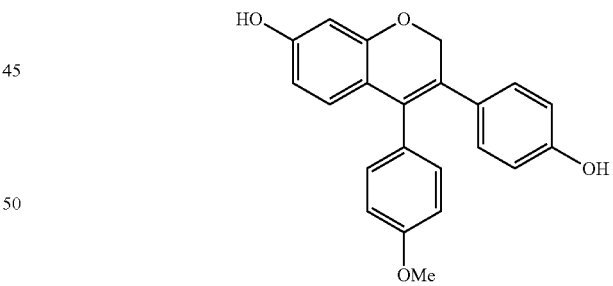

7-(tert-Butyldimethylsilyloxy)-3-(4-(tert-butyldimethylsilyloxy)phenyl)-4-(4-methoxyphenyl)chroman-4-ol (42 g), pTsOH (435 g), boiling chips and 2.5 L of ethanol were combined in a 2-neck 5 L round bottom flask with condenser attached. The reaction was heated at reflux for 3 hours. The solvent was concentrated in vacuo to ~100 ml before being poured into chilled, stirred water (700 ml). The mixture was then extracted with ethyl acetate, the combined organic layers washed with water (3×2 L), brine (1×500 ml), dried over anhydrous magnesium sulphate and filtered and solvent removed in vacuo to give red/brown oil. The oil was dissolved in methanol (~100 ml) and put in freezer overnight.

A white precipitate had formed overnight, which was filtered off and rinsed with methanol. The filtrate was concentrated in vacuo to give a brown oil.

Example 7

3-(4-Hydroxyphenyl)-4-(4-methoxyphenyl)-chroman-7-ol

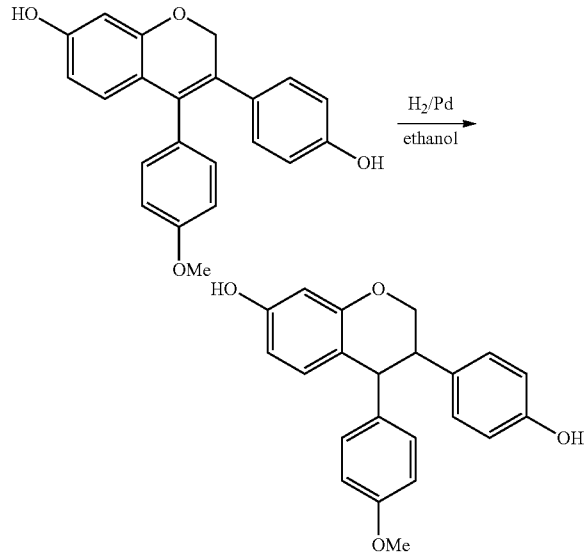

3-(4-hydroxyphenyl)-4-(4-methoxyphenyl)-2H-chromen-7-ol 25.5 g (70 mmoles), 10% Pd/Al$_2$O$_3$ 3.95 g and 200 ml of ethanol were combined in a 2-neck 500 ml round bottom flask. The reaction was hydrogenated at low pressure using standard conditions for 3 hours. The reaction was filtered through Celite to remove the catalyst, rinsed through with ethanol (300 ml). The filtrate was concentrated to ~50 ml before being poured into chilled, stirred water (1.4 L). A pale orange precipitate formed which then formed a brown oil. The mixture was then extracted with diethyl ether, the combined organic layers washed with water (3×1 L), brine (1×500 ml), dried over anhydrous magnesium sulphate and filtered. The solvent was removed in vacuo to give red/brown oil. The product was recrystallised from diethyl ether (~100 ml), to give brown solid which was rinsed with chilled diethyl ether to give off-white crystals 11.3 g. The 1H NMR spectrum and numbering scheme being shown below.

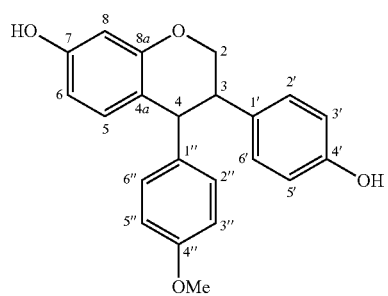 [SMILES: COc1ccc(C2c3ccc(O)cc3OCC2c2ccc(O)cc2)cc1]

| H | δ ppm | Peak Shape | J Hz | integrates | Comments |
|---|---|---|---|---|---|
| C2equatorial | 4.14 | Dd | 10.98 | 1 | |
| C2axial | 4.35 | Dd | | 1 | Dd is overlapping |
| C3 | 3.47 | Ddd | | 1 | |
| C4 | 4.20 | Dd | 5.12 | 1 | |
| C5 | 6.71 | D | 8.05 | 1 | |
| C6 | 6.36 | Dd | 2.56, 8.42 | 1 | |
| C8 | 6.41 | D | 2.20 | 1 | |
| C9 | 3.71 | S | — | 3 | |
| CT, C6' | 6.61 | D | — | 2 | Doublets overlapping for C2', C3', C2", C3" |
| C3', C5' | 6.61 | D | — | 2 | |
| C2", C6" | 6.61 | D | — | 2 | |
| C3", C5" | 6.61 | D | — | 2 | |
| | | | | | Total integration is 8 |

In the above general methods, the structures may be optionally substituted or protected with appropriate substituents, or synthons or derivatives thereof. The compounds may be present as, for example, their salts, acetates, benzyl or silyloxy derivatives as can be determined by a skilled synthetic chemist. Hydroxy groups can be readily alkylated (MeI/base), acylated (Ac$_2$O/Py) or silylated (Cl—SiR$_3$/base) and likewise deprotected by standard methods known in the art.

Example 8

Figure 12:
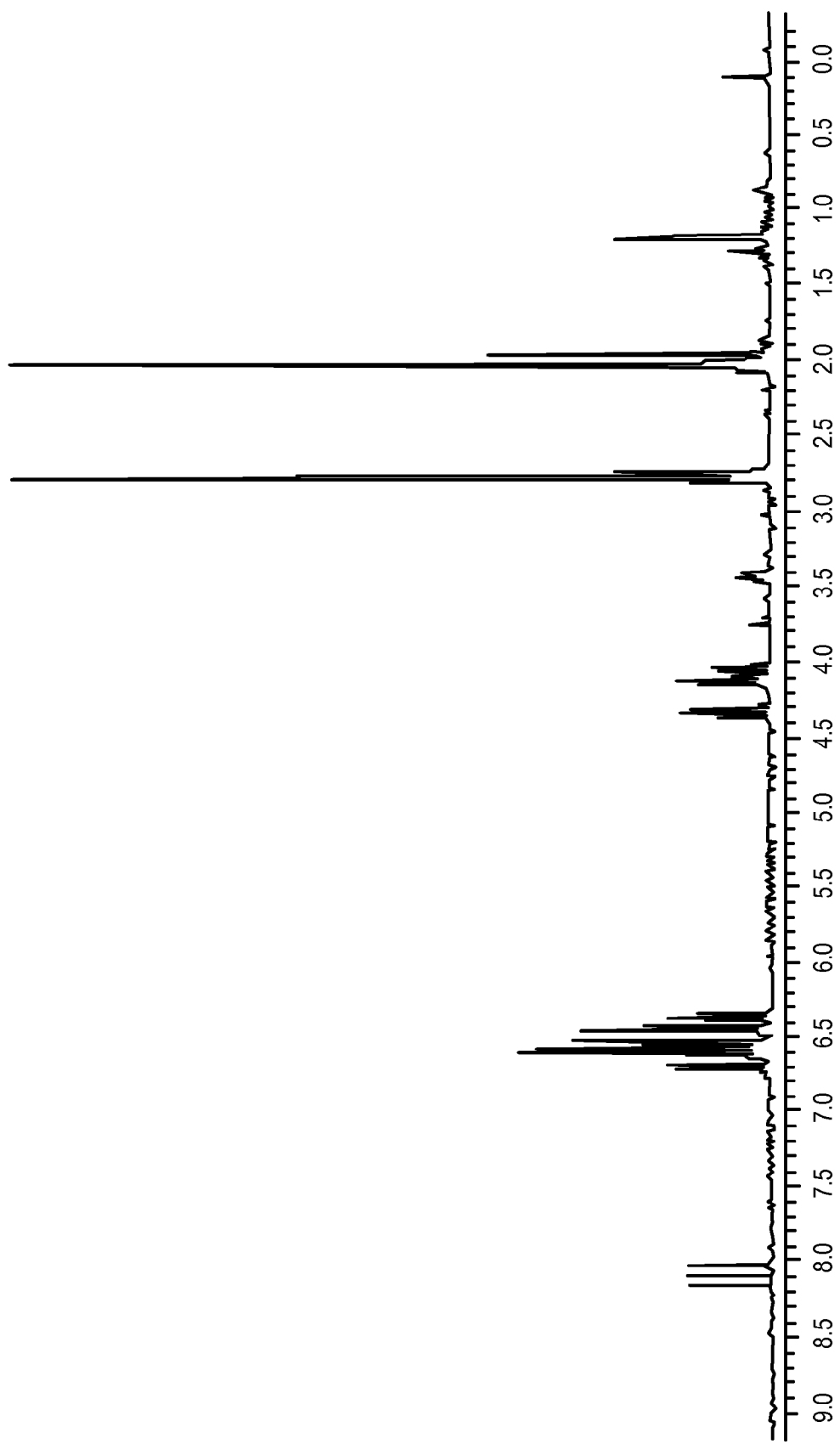
FIG. 12 represents the $^1$H n.m.r. spectrum of 3-(4-hydroxyphenyl)-4-(4-hydroxyphenyl)chroman-7-ol.

3-(4-Hydroxyphenyl)-4-(4-hydroxyphenyl)-chroman-7-ol 3-(4-hydroxyphenyl)-4-(4-methoxyphenyl)chroman-7-ol (3.17 g) was transferred to a round bottom flask and the flask was purged with nitrogen. 33 wt. % Hydrogen bromide in acetic acid (13 ml) was added drop-wise to the flask and the contents were heated to reflux at 130° C. for 7 hours. The reaction mixture was placed in an ice bath and adjusted to pH 6 using sodium hydroxide solution (40% w/v). The mixture was extracted with ethyl acetate and the ethyl acetate layer was further washed with water and brine prior to drying over magnesium sulphate. The mixture was filtered and the solvent was removed in vacuo to yield a brown solid (2.89 g). The solid was dissolved in minimal ethyl acetate and purified by column chromatography (Silica 60H, 200-400 mesh using ethyl acetate:chloroform (40:60) eluant). 3-(4-hydroxyphenyl)-4-(4-hydroxyphenyl)chroman-7-ol was obtained in ~80% purity and was further purified by semi-preparative high performance liquid chromatography (HPLC). The $^1$H n.m.r. is shown in FIG. 12.

2.0. Materials and Methods 2.1. Tissue Culture

The human pancreatic cancer cell line, HPAC (CRL-2119) was routinely cultured in 1:1 mixture DMEM (Dulbecco's Modified Eagle Medium Sigma) plus Ham's F12 (Sigma) medium containing HEPES (15 mM), insulin (0.002 mg/ml), transferrin (0.005 mg/ml), hydrocortisone, (40 ng/ml), epidermal growth factor (10 ng/ml). The ovarian cancer cell lines; CP70 was obtained as a gift from Dr. Gil Mor (Yale University) and cultured in a 1:1 mixture DMEM plus Ham's F12 medium, and SKOV-3 (ovarian cancer cell line) was purchased from ATCC and cultured in McCoys 5a medium. The breast cancer cell line MDA-MB-468 cultured in Leibovitz's L-15 medium. The melanoma cell line MM200 was obtained as a gift from Peter Hersey (University of Newcastle) and A2058 was obtained as a gift from Dr Peter Parsons (QIMR). Both were cultured in DMEM medium.

All cultures were supplemented with 10% FCS (fetal calf serum CSL, Australia), penicillin (100 U/ml), streptomycin (100 mg/ml), L-glutamine (2 mM) and sodium bicarbonate (1.2 g/L), and cultured at 37° C. in a humidified atmosphere of 5% $CO_2$. All cell lines were purchased from ATCC (Maryland, USA) except where noted.

The normal cell line NFF (neonatal foreskin fibroblasts) was a gift from Dr. Peter Parsons (Queensland Institute of Medical Research). RK (rabbit kidney) cells were obtained from Miller Whalley (Macquarie University). Both cell lines were cultured in RPMI supplemented with 10% FCS (CSL, Australia), penicillin (100 U/ml), streptomycin (100 mg/ml), L-glutamine (2 mM) and sodium bicarbonate (1.2 g/L), and cultured at 37° C. in a humidified atmosphere of 5% $CO_2$.

2.2. Proliferation Assays

IC50 values were determined for each cell line. Cells were seeded in 96-well plates at an appropriate cell density as determined from growth kinetics analysis and cultured for 5 days in the absence and presence of the test compounds. Cell proliferation was assessed after the addition of 20 μl of 3-4,5 dimethylthiazol-2,5-diphenyl tetrazolium bromide (MTT, 2.5 mg/ml in PBS, Sigma) for 3-4 hrs at 37° C. according to manufacturer's instructions. IC50 values were calculated from semi-log plots of % of control proliferation on the y-axis against log dose on the x-axis.

2.3. DHE and HMC Pharmacokinetics—Oral

HMC and DHE were prepared as homogenous suspensions in 1% CMC (m:v, water). Both formulations were delivered orally by savage to female BALB/c mice at a dosage of 50 mg/kg. Three animals were allocated to each timepoint (15 min, 30 min, 1 hr, 4 hr and 24 hr). At each respective timepoint, animals were euthanased by cervical dislocation and blood collected. Free HMC was analysed by mass spectroscopy.

2.4. HMC Pharmacokinetics—i.v. and i.p.

HMC was prepared as a solution in 20% hydroxypropyl-beta-cyclodextrin (m:v, water). The formulation was delivered either orally by gavage or by i.p. injection to female BALB/c mice at a dosage of 50 mg/kg. Three animals were allocated to each timepoint (15 min, 30 min, 1 hr, 4 hr and 24 hr). At each respective timepoint, animals were euthanased by cervical dislocation and blood collected. Urine was also collected and analysed for HMC. Free HMC was analysed by mass spectroscopy.

2.5 Pilot In Vivo Efficacy Study—HPAC Tumour Bearing Mice

Subconfluent (80%) flasks of HPAC cells were trypsinised, washed in Hanks balanced salt solution (Sigma), resuspended in dubellco's minimal essential medium (Sigma) and an equal volume of Matrigel™ (Becton Dickson) at a density of 3.7×$10^7$ cells per ml. Athymic nu/nu BALB/c mice were s.c. inoculated with 3.7×$10^6$ HPAC cells bi-laterally midway along the dorsal surface. For the HMC (n=3 per dosage regimen) and control groups (n=2), treatment commenced five days post inoculation to allow tumour formation. HMC was formulated 20% HPBCD and delivered i.p. daily for 15 days. The control group received equivalent (weight:weight) i.p. doses of 20% HPBCD. Tumour measurements commenced on day 5 post inoculation (10×10 $mm^2$) and were measured in 2 dimensions, length (a) and width (b), using calipers. Tumor weight (W) was calculated by the formula W=ab2/2, where a, is the longer of the 2 measurements (Odwyer et al., 1994). Tumour proliferation curves were analyzed with respect to maximal tumour inhibition (treated/control, T/C). On sacrifice, liver, kidney, femur, stomach and colon tissue were fixed in buffered formalin, embedded in paraffin, sections cut and stained with H&E. Stained sections were then submitted to Rothwell consulting for histopathology analysis. Serum biochemistry was conducted on bloods taken from control, vehicle control and HMC treatment groups. Serum analysis was conducted by Veterinary Clinical pathology (U. Syd).

2.6 Three-D Model Analysis of Synergy

3-D model analysis of the cytotoxic interaction between drug A and drug B enables the representation of predicted inhibitory effect of two drugs in combination in 3 dimensions to reveal actual regions of synergy or antagonism. The 3D synergy plots are based on a theory of "Theretical Additivity" (TA) as outlined by Kanzawa et al (Int. J. Cancer 71, 311-319 (1997)). Theoretical Additivity was calculated from the cytotoxicities of drug A and drug B as monotherapies using the following formula which assumes the drugs are mutually exclusive inhibitors:

$$TA_{(1)} = \frac{(f_a)A + (f_a)_B - 2(f_a)A(f_a)_B}{1 - (f_a)_A(f_a)_B}$$

Where: $(f_a)_A$=fraction of cells affected by drug A
$(f_a)_B$=fraction of cells affected by drug B The TA is calculated for each combination of drug concentrations and subtracted from the observed experimental effect for each combination to give a measurement of synergistic action. A positive difference indicates that more cells are affected by the drug combination than would be expected in theory if the two drugs were administered together—hence synergism. A negative difference indicates that less cells were affected than theoretically expected—hence antagonism.

3.0. Results

3.1. Normal Cell Toxicity

Dehydroequol (DHE) was less toxic to both NFF and rabbit kidney cells with IC50 values above 150 μM when compared to HMC (86 and 61 μM respectively) (Table 1 and FIG. 1). In a separate study, HHC was found to be non-toxic to both NFF and RK cells (see again Table 1). When compared to cisplatin, a benchmark chemotherapeutic agent, the degree of toxicity exhibited by HMC and HHC is mild.

TABLE 1

Relative toxicity of DHE, HMC, HHC and cisplatin against Neonatal foreskin fibroblasts (NFF) and rabbit kidney cells.

| Tissue/cell | | Analogue (IC50 μM) | | | Antineoplastic (IC50 μM) |
|---|---|---|---|---|---|
| Type | Designation | DHE | HMC | HNC | Cisplatin |
| Fibroblast | Neonatal Foreskin Fibroblasts (Human, NFF) | >150 | 86.12 ± 7.6 | 60.8 | 9.85 ± 5 |
| Kidney | Rabbit Kidney | >150 | 61 ± 4.3 | >150 | Not tested |

3.2. In Vitro Efficacy Against Cancer Cells

Figure 2:
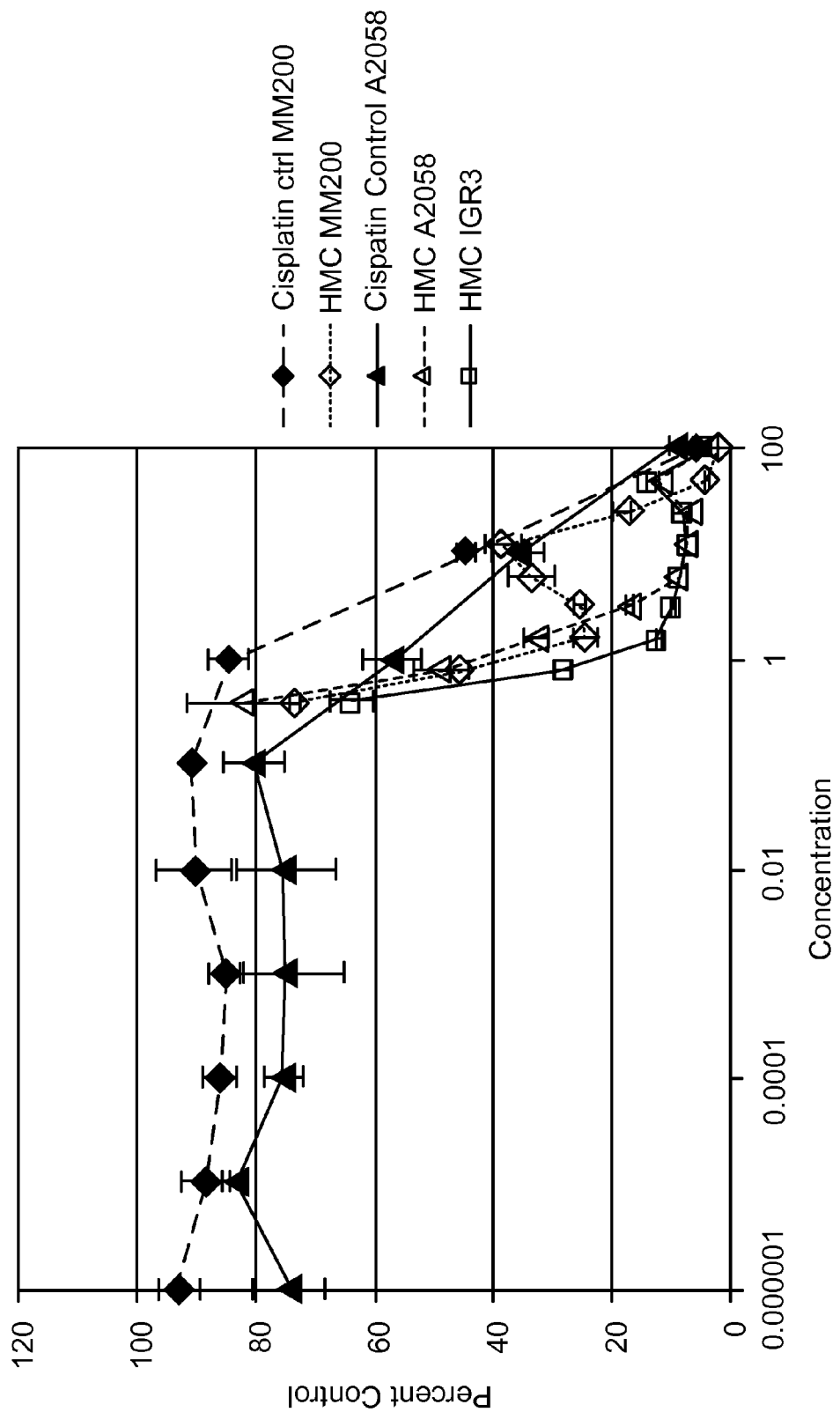
FIG. 2 represents HMC efficacy in melanoma cells in comparison with cisplatin.

When compared to DHE IC50 values, HMC demonstrated markedly superior activity (~5-10 fold greater) against the multi-drug resistant, p53 mt ovarian cancer cell line (SKOV-3), the AR negative, p53 Mt prostate cancer cell line (PC3), both ER positive (p53 wt) and negative (p53 mt) breast cancer cell lines (MCF-7 and MDA-MB-468 respectively), p53 Mt Glioma (HTB-138), p53 Mt pancreatic cancer (HPAC) and p53 Mt large cell lung cancer (Table 2). HMC exhibited anti-cancer activity comparable to that of DHE against all other cell lines tested. (Table 1). Particular efficacy of HMC was noted against melanoma cells. (Table 2.1 and FIG. 2). This represents a substantial advantage over the prior art.

HMC was differentially active against 2 separate colorectal cell lines, with marked activity observed against HT-29 cells and somewhat less activity against HCT-15. It is noted that HT-29 and HCT-15 are COX-2 positive and deficient respectively. When examined microscopically and compared to cells treated with vehicle only, HMC treated SKOV-3 cells exhibited morphological changes consistent with cells undergoing apoptosis (cell enlargement, granular appearance in cytosol and blebbling of plasma membrane). In contrast SKOV-3 cells exposed to 100 μM Dehydroequol after 18 hr retained a relatively normal morphology, comparable with that of vehicle only treated cells.

TABLE 2.1

Comparison of Dehydroequol and HMC cytoxicity against cell lines representative of different malignancies.

| Indication | Designation | Analogue (IC50 μM) DUE | Analogue (IC50 μM) HMC | Antineoplastic (IC50 μM) Cisplatin |
|---|---|---|---|---|
| Ovarian | A2780 | 1.7 ± 0.61 | 1.58 ± 0.59 | 2.10 |
|  | CP70 | 1.69 ± 0.62 | 1.21 ± 0.29 | 10.30 |
|  | SKOV-3 | 21.83 ± 4.65 | 2.26 | 5.40 |

TABLE 2.1-continued

Comparison of Dehydroequol and HMC cytoxicity against cell lines representative of different malignancies.

| Indication | Designation | Analogue (IC50 μM) DUE | Analogue (IC50 μM) HMC | Antineoplastic (IC50 μM) Cisplatin |
|---|---|---|---|---|
| Prostate | PC3 | 9.09 ± 8.12 | 2.50 ± 0.92 | 2.11 |
|  | LNCaP | 4.8 ± 3.8 | 4.52 | >10 |
|  | DU145_ | 5.95 ± 1.5 | 3.78 | 2.07 |
| Breast | MCF-7 | 21.5 ± 13.2 | 7.15 ± 7 | 3.69 |
|  | MDA-MB-468 | 7.9 ± 3.5 | 1.1 ± 0.35 | 0.58 |
| Glioma | HTB-138 | 7.35 ± 0.89 | 1.9 ± 0.27 | 42.30 |
| Pancreatic | CRL-2119 | 56.62 ± 16.8 | 14.1 ± 1.16 | 9.36 |
| Leukemic | RPM1-8226 | 3.72 ± 0.08 | NT | NT |
|  | CCRF-CEM | 1.7 ± 0.68 | 1.90 | NT |
| Lung | NCI-H23 | 8.75 ± 7.2 | 3.75 ± 2.5 | NT |
|  | NCI - H460 | 10.6 ± 3.8 | 2.23 ± 0.15 | 22.29 |
| Colorectal | HT-29 | 50.45 ± 21.9 | 3.7 ± 1.4 | 22.7 ± 35 |
|  | HCT-15 | 24.4 ± 12.57 | 37.8 ± 33 | 129.9 ± 39 |
| Melanoma | MM200 | 2.90 | 0.7 ± .03 | 8.3 ± 0.7 |
|  | A2058 | NT | 1.2 ± 0.65 | 5.73 ± 2.3 |
|  | IGR-3 | NT | 0.53 ± 0.02 | NT |

In further studies, the cytotoxicity of various compounds described herein against various cell lines was determined. Compound 14-ene is the 3-ene chromene precursor to the correspondingly reduced chroman, compound 14. It was observed that compounds 1, 2 and 11 show the best efficacy against most all cancer cell lines. Compound 14 shows slightly better efficacy in general compared to its corresponding 14-ene and to compound 6 (Table 2.2).

TABLE 2.2

Chroman compounds 1, 2, 6, 11 and 14 and chrom-3-ene compound 14-ene cytoxicity against cell lines representative of different malignancies.

| Indication | Cell line | HMC 1 | 2 | 6 | HHC 11 | 14-ene | 14 |
|---|---|---|---|---|---|---|---|
| Ovarian | CP70 | 2.1 | 3 ± 1.2 | >100 | 1.1 ± 0.9 | >100 | >100 |
| Prostate | PC3 | 2.5 ± 1 | 4.2 ± 0.02 | 116 ± 57 | 0.88 ± 0.4 | 46.2 ± 7 | 32.5 ± 2.1 |
| Breast | MDA-MB-468 | 2.8 ± 4.2 | 1.9 | 28.7 ± 3.6 | 1 ± 0.1 | NT | 56.6 |
| Glioma | HTB-138 | 1.9 ± 0.3 | 3.77 | >100 | 0.52 ± 0.1 | 8.2 ± 10 | 53.5 ± 14 |
| Pancreatic | HPAC | 2_8 ± 0.9 | 24.4 ± 12 | >100 | 31.6 ± 27 | 81.5 ± 59 | 79 ± 56 |
| Leukaemia | CCRF-CEM | 2 ± 0.97 | 4.02 | 92 ± 81.6 | 0.6 ± 0.01 | >100 | 73 ± 51.6 |
| NSC Lung | NCI-E460 | 2.8 ± 2 | 5.4 ± 2.1 | NT | 0.5 ± 0.1 | >100 | 65 |
| Colorectal | HT-29 | 5.4 ± 1.8 | 59.4 | >100 | 2.5 ± 1 | 97.5 ± 30 | 45 ± 4.7 |
| Melanoma | MM200 | 1.07 ± 0.5 | 7.34 | >100 | 0.6 ± 0.3 | 58 ± 2.7 | 93 ± 2.9 |

3.3.1. HMC Pharmacokinetics—Oral

Figure 3:
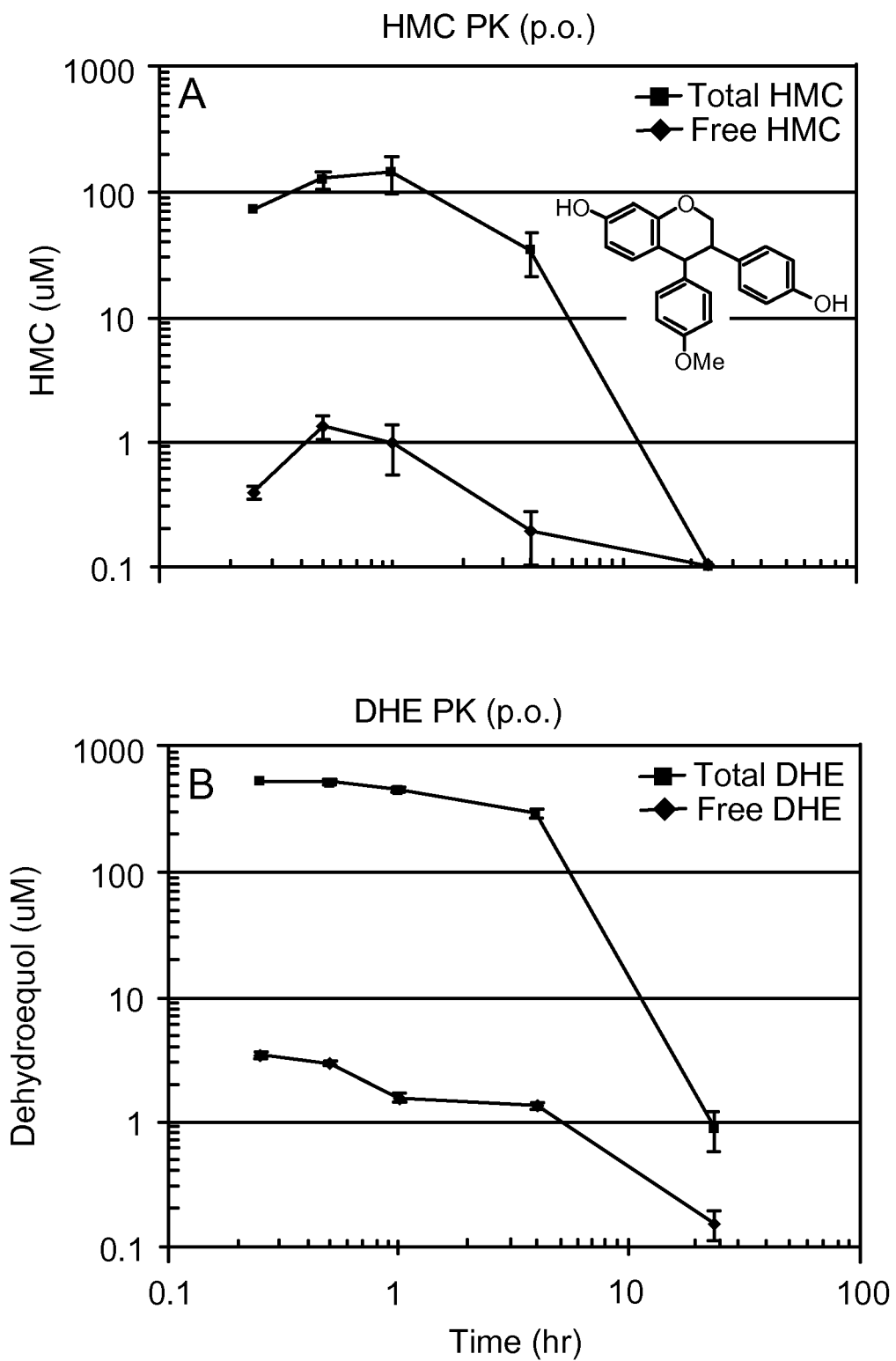
FIG. 3 represents a pharmacokinetic profile of free and total forms of HMC (A) and DHE (B) after p.o (peri oral) administration to BALB/c mice (50 mg/kg).

When compared with the pharmacokinetic profile of orally dosed DHE, HMC administered via the same route and dosage (50 mg/kg), HMC exhibited a Cmax of 141 µM (achieved after 1 hr) compared to 511 µM for DHE (achieved after 15 min) (Table 3 and FIG. 3). Like DHE, HMC is also subject to conjugation with low plasma concentrations of the free form of the molecule observed (1.3 µM after 30 min) (Table 3 and FIG. 3). This is less than half the maximum concentration of free dehydroequol achieved using the same dosage regimen (3.3 µM after 15 min) (FIG. 3). The ratio of free:total is greater for HMC when compared to DHE (0.92 vs 0.64 respectively).

TABLE 3.1

Comparison of free and total plasma concentrations achieved in mice dosed with 50 mg/kg of either HMC or DHE p.o.

| | HNC (µM) | | DHE (µM) | |
|---|---|---|---|---|
| Time | Total | Free | Total | Free |
| 0.25 | 72 ± 4.4 | 0.38 ± 0.04 | 511.5 ± 99 | 3.3 ± 0.13 |
| 0.5 | 122 ± 18.4 | 1.3 ± 0.2 | 357 ± 82 | 2.9 ± 0.05 |
| 1 | 141 ± 45.8 | 0.95 ± 0.4 | 387 ± 22.8 | 1.5 ± 0.11 |
| 4 | 33.9 ± 12.7 | 0.19 ± 0.08 | 117.6 ± 42 | 1.3 ± 0.07 |
| 24 | 0 | 0 | 0.13 ± 0.1 | 0.15 ± 0.04 |

3.3.2. HMC and HHC Pharmacokinetics—Oral

Human patients were orally dosed with 200 mg of either HMC or HHC. For each challenged patient, blood was taken over a 6 hour period and the results averaged to characterise the plasma pharmacokinetics. The initial results give an oral half-life of 3.99 hours for HMC and 3.26 hours for HHC (Table 3.2).

TABLE 3.2

Comparison of plasma half-life concentrations achieved in humans dosed with 200 mg of either HMC or HHC

| Compound | $C_{max}$ (ng/mL) | $T_{max}$ (h) | $T1_{1/2}$ (h) |
|---|---|---|---|
| HMC (1) | 513 | 2.17 | 3.99 |
| HHC (11) | 341 | 2.67 | 3.26 |

3.4. HMC Pharmacokinetics—i.v. and i.p.

Figure 4:
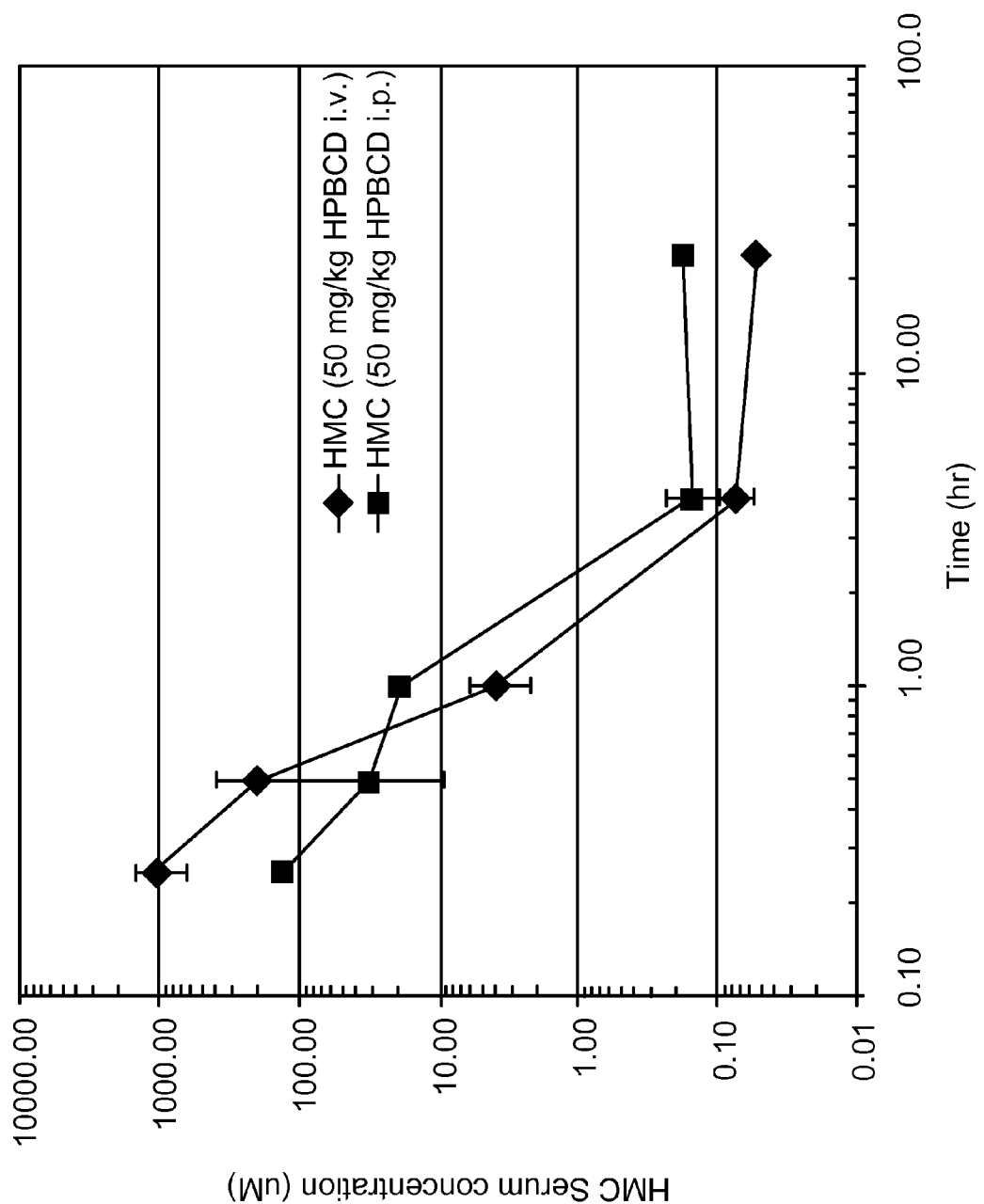
FIG. 4 represents a comparison of the pharmacokinetic profile the HMC concentration in serum after i.v (intravenously) and i.p (intraperitoneally) administration of HMC formulated in 20% hydroxypropyl-beta-cyclodextrin at a dose of 50 mg/kg.

When formulated in HPBCD and delivered i.v., extremely high levels of HMC were observed in the blood equating to 1 mM of drug, 15 min post administration (FIG. 4). Elimination kinetics of i.v. delivered HMC were biphasic with HMC being rapidly excreted from blood at a rate of 1000 µM/hr in the first hr post administration. Assuming linear excretion, this rate slowed to 0.97 µM/hr in hours 1-4 hr post administration. When the same formulation was administered i.p., approximately 1 log less HMC was observed in plasma (131 µM by i.p. administration vs 1069 µM by i.v. administration) up to 1 hour post administration (FIG. 4). Elimination kinetics by i.p. administration however, was much slower during this period (112 µM/hr) thus resulting in a serum concentration some 4.5 fold higher at 1 hr post administration (18.7 by i.p. vs 3.98 by i.v.). Conversely, in hours 1-4 post administration, elimination kinetics was faster after i.p. administration when compared to i.v. (4.6 µM/hr by i.p. vs 0.97 µM/hr by i.v.). These data confirm that HMC is highly bioavailable in its free state when administered by i.v. or i.p. routes. In conjunction with oral PK data, these data also suggest that HMC is susceptible to rapid removal by GI detoxification enzymes. Large concentrations of free HMC were observed in urine over 0.5, 1 and 4 hr where collected (3.3 mM, 3.9 mM and 0.093 mM).

TABLE 4

Comparison of the pharmacokinetic profile of HMC in serum after i.v and i.p administration of HMC formulated in 20% hydroxypropyl beta cyclodextrin at a dose of 50 mg/kg).
Inset shows HMC concentrations in serum.

| | Serum HMC (µM) | |
|---|---|---|
| Time (hr) | iv | ip |
| 0.25 | 1069.75 | 131.37 |
| 0.50 | 198.66 | 31.78 |
| 1 | 3.98 | 18.74 |
| 4 | 0.07 | 0.15 |
| 24 | 0.05 | 0.17 |

3.5. Pilot In Vivo Efficacy Study—HPAC Tumour Bearing Mice

Figure 5:
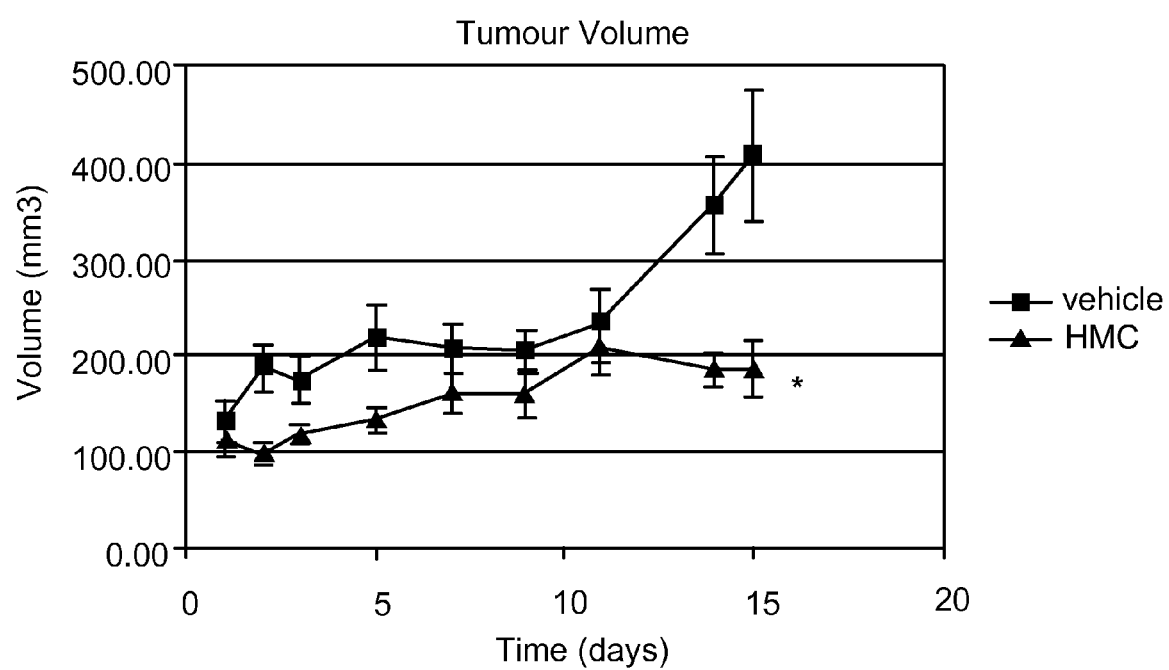
FIG. 5 represents comparative mean tumour volume data taken from nude mice bearing HPAC pancreatic cancer tumours treated with either i.p dosed 20% HPBCD (vehicle control, qdx15) or HMC (100 mg/kg, qdx15). Data represented as mean±SEM*, student's T-test, p<0.01.
Figure 6:
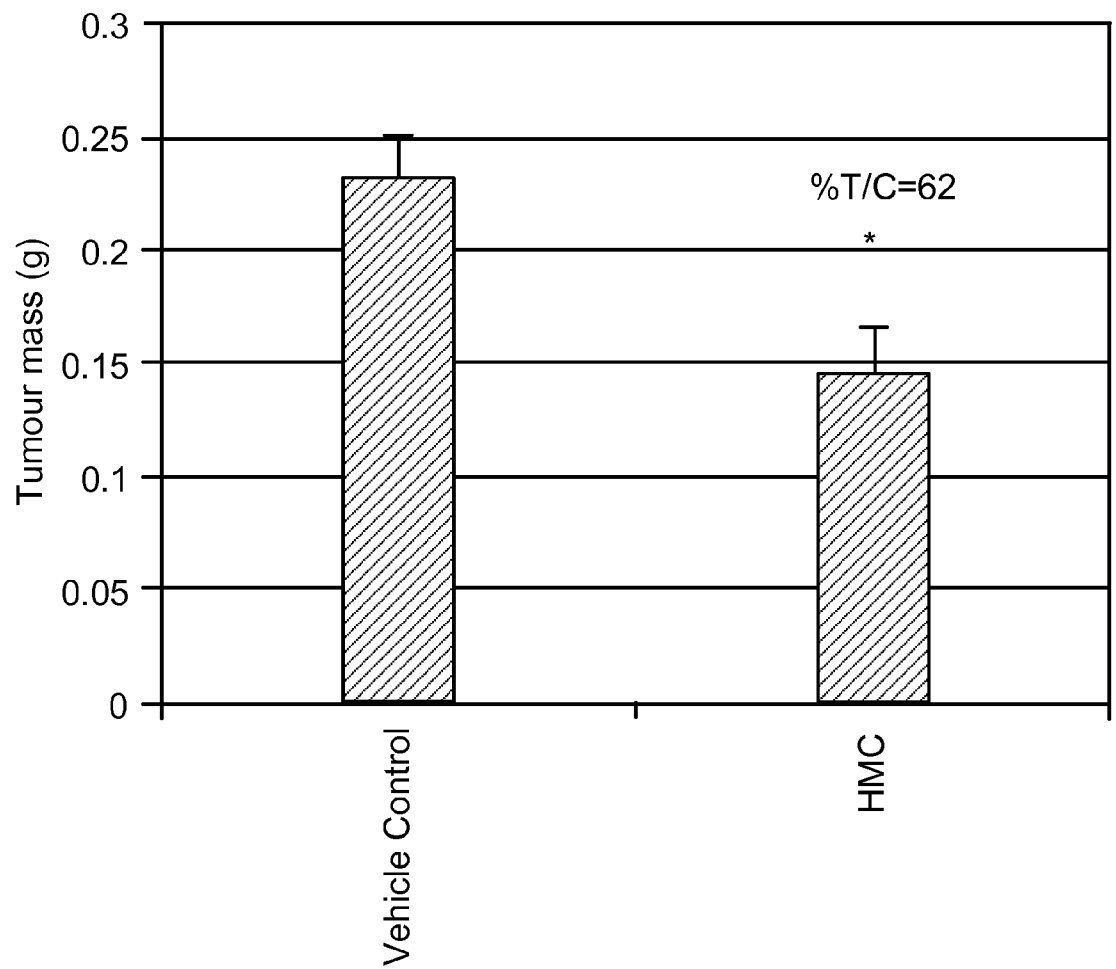
FIG. 6 represents comparative mean terminal tumour mass data taken from nude mice bearing HPAC pancreatic cancer tumours treated with either i.p dosed 20% HPBCD (vehicle control, qdx15) or HMC (100 mg/kg, qdx15). Data represented as mean±SEM*, student's T-test, p<0.01.
Figure 7:
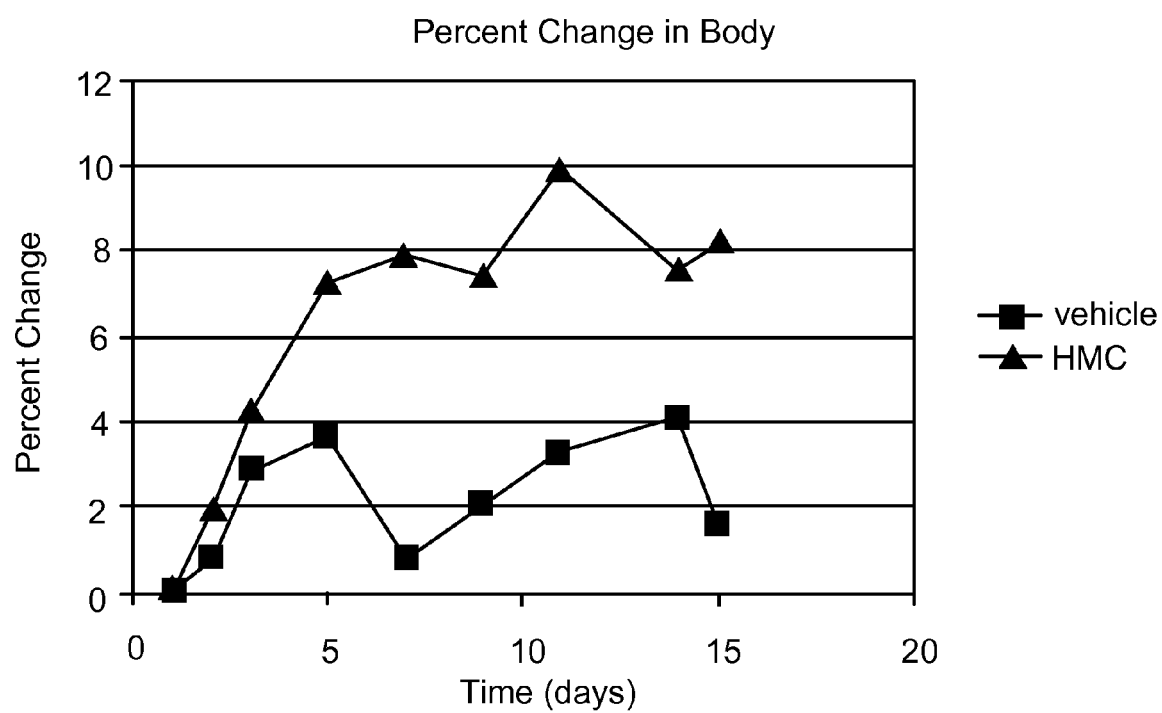
FIG. 7 represents comparative mean terminal tumour mass data taken from nude mice bearing HPAC pancreatic cancer tumours treated with either i.p dosed 20% HPBCD (vehicle control, qdx15) or HMC (100 mg/kg, qdx15). Data represented as mean±SEM*, student's T-test, p<0.01.

HMC when dosed daily, i.p. at 100 mg/kg significantly retarded the proliferation of HPAC tumours over the treatment period when compared to vehicle control (FIG. 5). When the mean terminal tumour mass was assessed a significant reduction in final tumour burden (% T/C=62) was also noted (FIG. 6). Importantly, no signs of toxicity were noted in animals dosed with HMC at 100 mg/kg daily for 15 days as determined by weight loss. Indeed animals treated with HMC appeared to thrive when compared to control (FIG. 7). Organs (liver, kidney, spleen, femur, stomach and colon) were collected and submitted for histopathological assessment by Bothwell consulting. A limited serum biochemistry analysis was also conducted. These data confirm that HMC demonstrates antitumorigenic activity against HPAC tumours in vivo.

3.5.1. Histopathological Examination of HMC Treated Groups

Histopathological examination of haematoxylin and eosin-stained sections cut from formalin-fixed tissues from two series of experimental mice was made. The liver, kidney, stomach and colon were examined for evidence of toxic damage, the spleen and bone marrow for evidence of myelosuppression and the tumour for degree of necrosis. A score of 0-5 was allocated to each tumour specimen for the degree of necrosis present, a 0 score representing, no necrosis and a score of 5, total necrosis. The sections were scored 'blind' on two separate occasions and the final score given in the results is the mean of these two scores.

TABLE 5

HMC Toxicology

| Sample | Description | Necrosis Score 0-5 |
|---|---|---|
| 4/04 & 1/8 | Vehicle control | 0.5 |
| 4/04 & 2/8 | HMC | 2 |
| 4/04 & 4/5 | | 2 |

TABLE 5-continued

HMC Toxicology

| Sample | Description | Necrosis Score 0-5 |
|---|---|---|
| 4/04 & 5/8 | | 2 |
| 4/04 & 1/11 | No treatment control | 0.5 |

3.5.1.1. Overview of Results

No evidence of toxicity or myelosuppression was detected in sections cut from the tissues of the drug-treated mice. However, in all the drug-treated mice there were patchy mild/moderately severe chronic inflammatory changes affecting the serosa and attached mesentery, as well as reactive changes of the mesothelial cells, in some of the tissues examined. These changes are consistent with the intra-peritoneal injection of a mildly irritant material.

Significant necrosis of tumour tissue was not detected in control specimens 1/8 and 1/11. However, there was considerable necrosis in the tumour sections from the drug-treated mice.

3.5.1.2. Serum Biochemistry of HMC Treated Mice in Comparison to Control

Alakalines phosphatase (ALP), alanine transferase (ALT) and creatine (Cre) were assessed in HMC treated vs control animals. ALP and Cre levels were similar to control and fell within normal ranges (for rat) however, ALT levels in vehicle control and HMC treated groups were much lower than no treatment control levels.

TABLE 6

Serum biochemistry of HMC treated mice in comparison to control

| | | Clinical marker (mice) | | | |
|---|---|---|---|---|---|
| Sample | Group | ALP U/L | ALT 1.8 L | Cre μM | Urea mM |
| Control | 1/11 | U/L | 713 | 7 | 9.92 |
| Vehicle control | 1/8 | 152 | 441 | 26 | 9.81 |
| HMC treated | 2/8 | 74 | 505 | 17 | 7.27 |
| (100 mg/kg) | 4/8 | 111 | 482 | 8 | 8.11 |
| | 5/8 | 100 | 494 | 6 | 7.79 |
| Normal ranges) | | 86-246 | 84-143 | 1.5-6 | 6.3-8* |

*for rat
ALP: Alkaline phosphatase
ALT: Alanine aminotransferase
Cre: Creatinine

3.6. HMC Induced Apoptosis in Melanoma Cells and Normal Fibroblasts

3.6.1. Melanoma

Figure 8A:
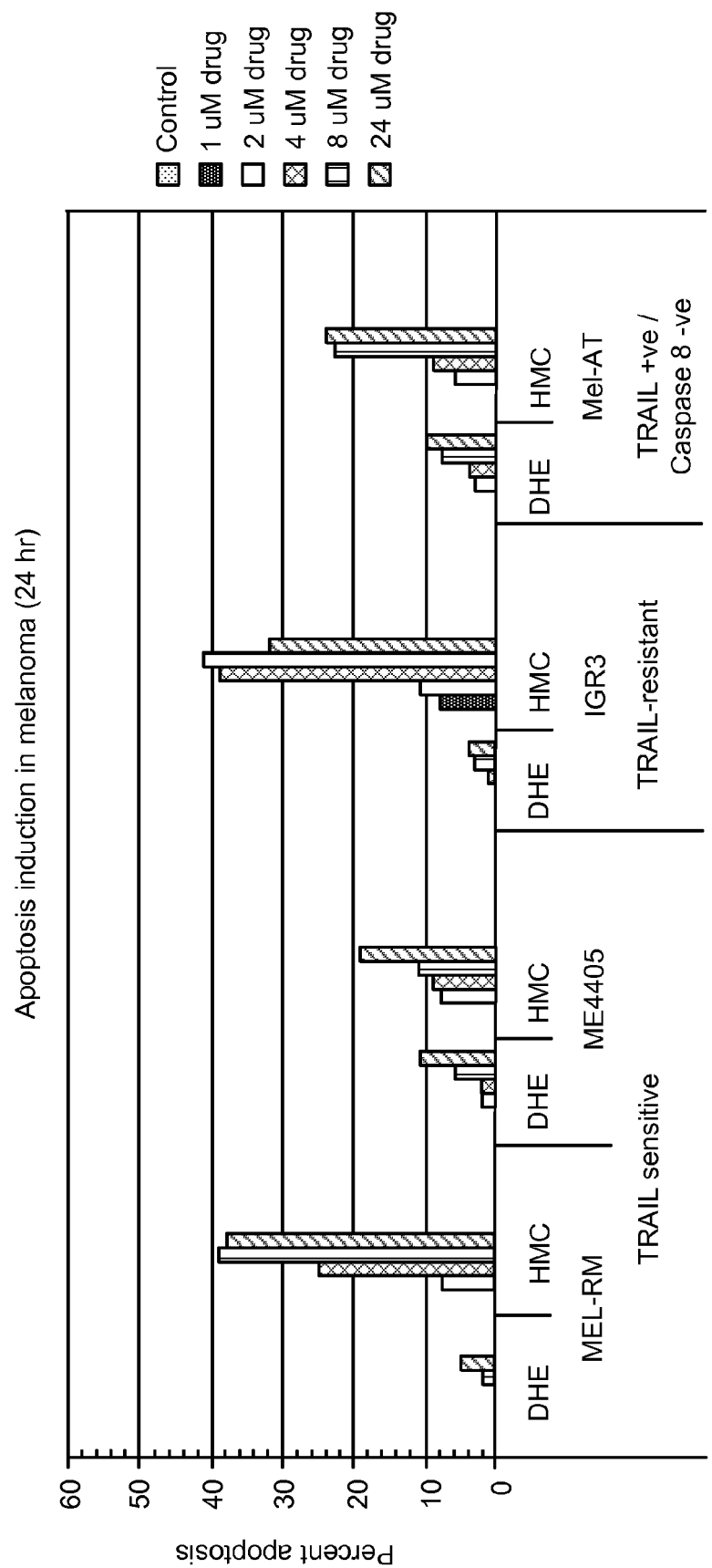
FIG. 8 represents a summary of apoptosis incidence in DHE and HMC treated melanoma cells over a 24 and 48 hour period.
Figure 8B:
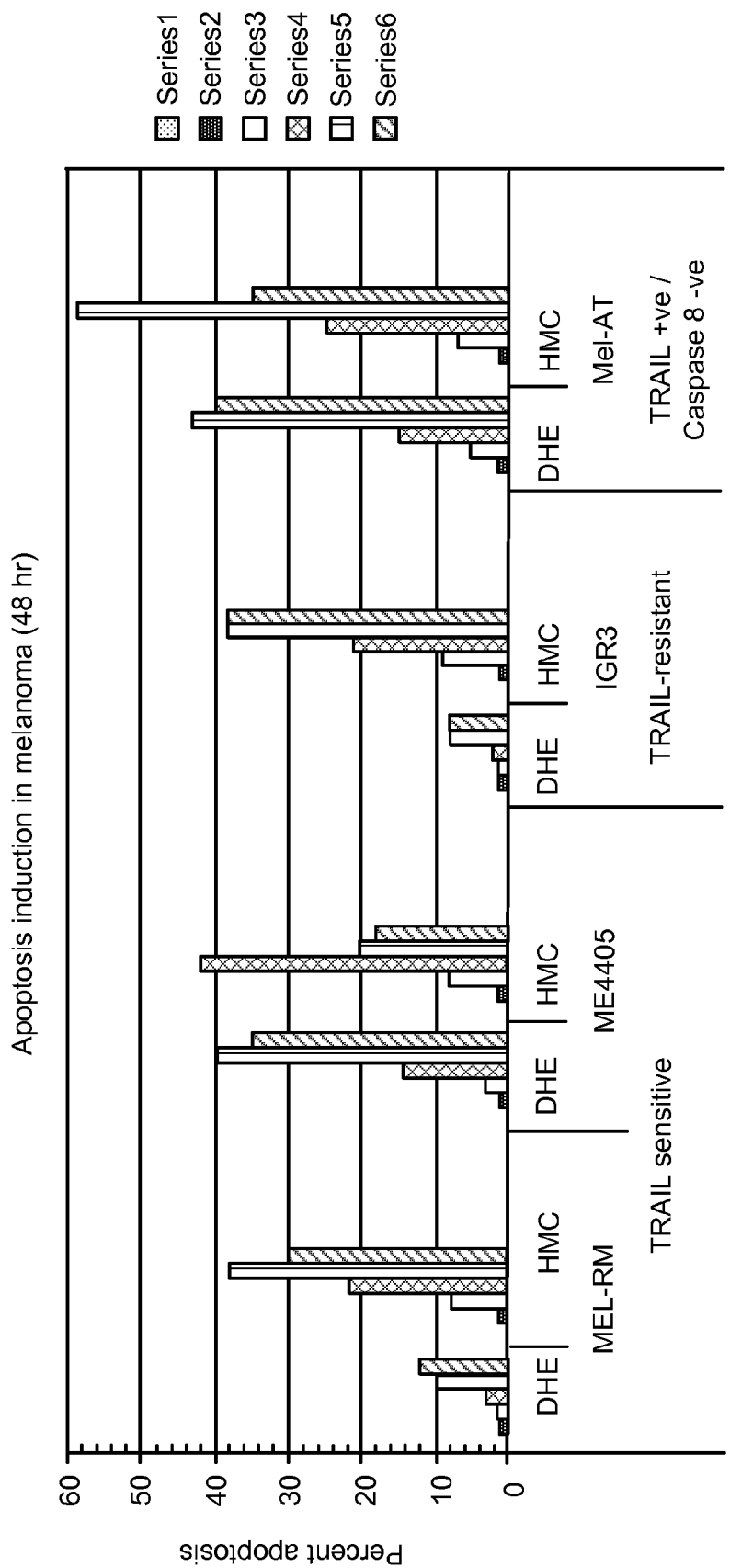

HMC induced apoptosis in all TRAIL-sensitive and -resistant melanoma cells at concentrations down to 2 μM (~7-10% apoptosis) over 24 and 48 hrs of exposure (Table 7 and FIG. 8A). At the clinically significant drug concentration of 4 μM, the incidence of apoptotic cells after 24 hr exposure to HMC rose to 25% and 39% in TRAIL sensitive (MEL-RM) and TRAIL negative (IGR3) cell lines respectively (Table 7 and FIG. 8A). The incidence of HMC induced apoptosis at 4 μM after 24 hr exposure in the other cell lines was ~9%. In comparison, the incidence apoptosis in DHE-treated cells at a concentration of 4 μM after 24 hr exposure was 0-1%. Over 48 hr at the same concentration of HMC (4 μM), the incidence of apoptosis rose to 21-42% in all cell lines examined (Table 7 and FIG. 8B). DHE was the only other agent to induce moderate levels of apoptosis after 48 hr exposure at a concentration of 4 μM, but only in ME4405 (14%) and Mel-AT (15%) cell lines (Table 7 and FIG. 8B).

TABLE 7

Summary of apoptosis incidence in DHE and HMC treated melanoma cells over 24 and 48 hr.

| | | Percent Apoptosis | | | | | | | |
|---|---|---|---|---|---|---|---|---|---|
| Drug Concen-tration | | TRAIL sensitive | | | | Trail-resistant | | Trail +ve/ Caspase 8 −ve | |
| | | MEL-RM | | ME4405 | | IGR3 | | Mel-AT | |
| (μM) | | DHE | HMC | DHE | HMC | DHE | HMC | DHE | HMC |
| 24 hr expo-sure | Con-trol | 0 | 0 | 0 | 0 | 0 | 0 | 0 | 0 |
| | 1 | 0 | 0 | 0 | 0 | 0 | 8 | 0 | 0 |
| | 2 | 0 | 8 | 2 | 8 | 0 | 11 | 3 | 6 |
| | 4 | 0 | 25 | 2 | 9 | 1 | 39 | 4 | 9 |
| | 8 | 2 | 39 | 6 | 11 | 3 | 41 | 8 | 23 |
| | 20 | 5 | 38 | 11 | 19 | 4 | 32 | 10 | 24 |
| 48 hr expo-sure | Con-trol | 0 | 0 | 0 | 0 | 0 | 0 | 0 | 0 |
| | 1 | 1 | 1.5 | 1 | 1.5 | 1 | 1 | 1.5 | 1 |
| | 2 | 1.5 | 8 | 3 | 8 | 1 | 9 | 5 | 7 |
| | 4 | 3 | 22 | 14 | 42 | 2 | 21 | 15 | 25 |
| | 8 | 10 | 38 | 40 | 20 | 8 | 38 | 43 | 59 |
| | 20 | 12 | 30 | 35 | 18 | 8 | 38 | 40 | 35 |

3.6.2. Normal Fibroblasts

Figure 9:
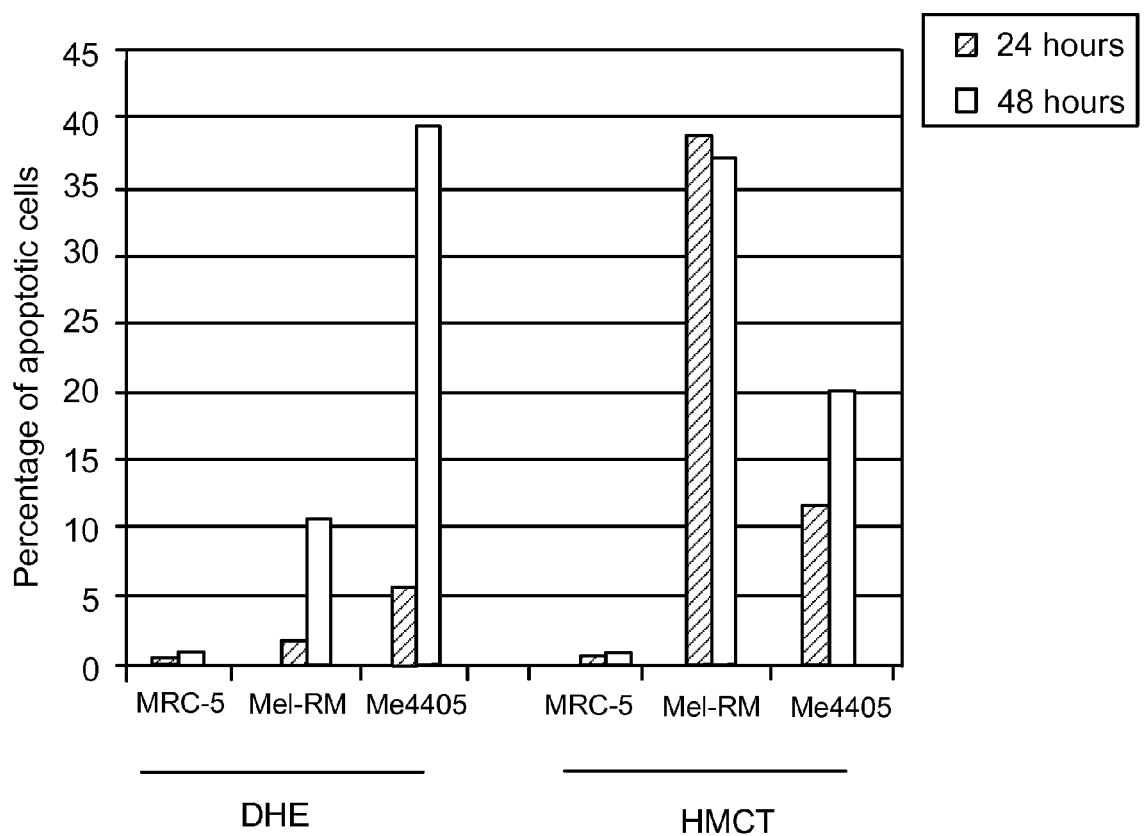
FIG. 9 represents selective initiation of programmed cell death in HMC and DHE treated malignant melanoma cells (Mel-RM and Me4405). The same concentration of DHE and HMC and exposure times do not induce apoptosis in normal fibroblasts (MRC-5).

Studies were conducted on normal fibroblasts (MRC-5) and TRAIL-sensitive melanoma cells (ME4405 and MEL-RM) using 8 μM of either DHE or HMC over 24 and 48 hr of exposure (FIG. 9). These data demonstrate that HMC, and to a lesser extent DHE, induced marked levels of apoptosis in both melanoma cell lines over 24 and 48 hr. Importantly, while promoting programmed cell death in malignant cells, normal fibroblasts were shown to both HMC and DHE induced apoptosis at 8 μM drug over 24 and 48 hr of exposure. These data confirm that HMC is selectively cytotoxic to cancer cells.

The isoflavan compounds of the invention exhibit a superior efficacy profile against all cancers tested when compared to DHE. While HMC is marginally more toxic than DHE in NFF and RK cells, HMC is markedly less toxic than cisplatin. HMC delivered orally in mice is less bioavailable when compared to DHE but the ratio of free:total is greater. HPBCD-formulated HMC was markedly bioavailable in its free form when delivered i.v and i.p. Significant serum concentrations of free HMC post-delivery i.p. were some 18 fold above that of orally delivered HMC. It has been demonstrated that HMC, formulated in 20% HPBCD and delivered i.p., exerts a moderate antitumorigenic activity against HPAC tumours in vivo. HMC when delivered at 100 mg/kg to mice is not toxic to major organs as determined by histopathology however, in all the drug-treated mice there were patchy mild/moderately severe chronic inflammatory changes affecting the serosa and attached mesentery, as well as reactive changes of the mesothelial cells which are consistent with the intra-peritoneal injection of a mildly irritant material.

HMC induced moderate-strong levels of apoptosis in TRAIL-resistant and TRAIL-sensitive melanoma cells after both 24 and 48 hrs of exposure. Normal fibroblast cells were resistant to apoptosis after 48 hrs exposure DHE induces mild-moderate levels of apoptosis in TRAIL-resistant and TRAIL-sensitive melanoma cells after 48 hrs of exposure. Normal fibroblast cells were resistant to apoptosis after 48 hr exposure. The ability of both HMC and DHE to induce apoptosis in caspase negative cells suggest that an operational extrinsic programmed cell death pathway is not essential for HMC and DHE mediated apoptosis.

3.7 In Vitro HMC Synergistic Toxicity in Cancer Cells when Combined with Cisplatin, Paclitaxel and Gemcitabine, Camptothecin, Topotecan and Doxorubicin

3.7.1. HMC Combination with Cisplatin Against the MM200 Melanoma Cell Line

Figure 11:
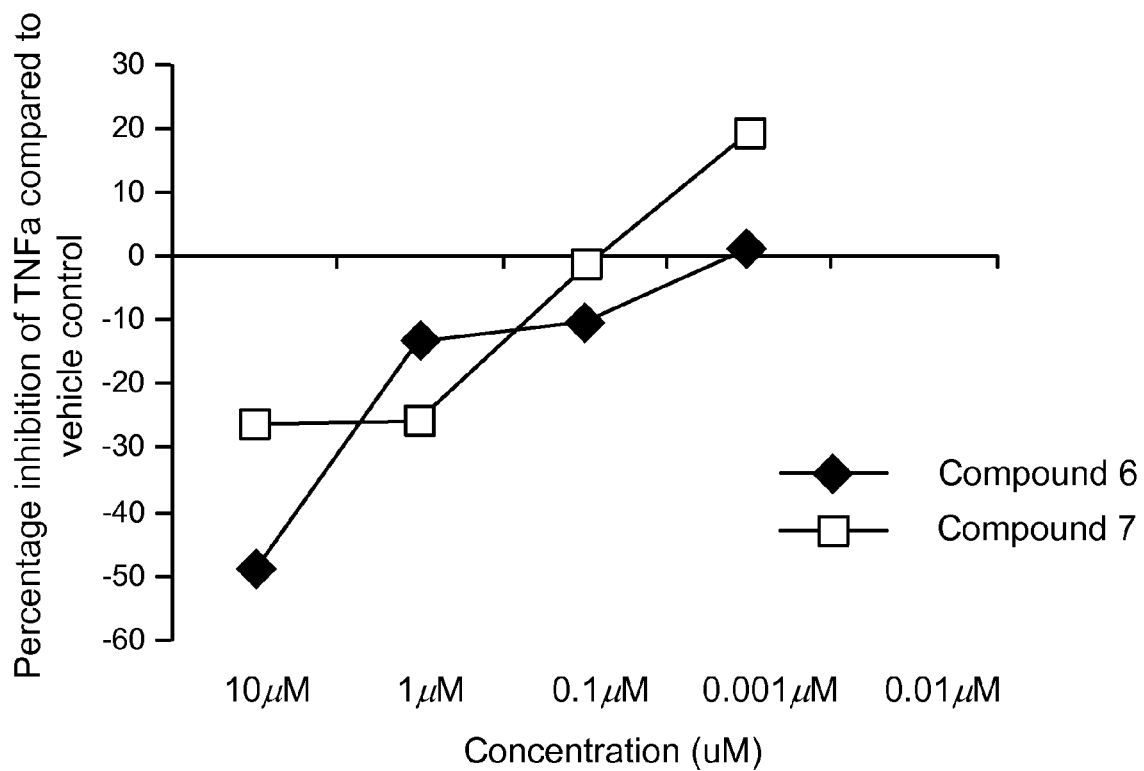
FIG. 11 represents the percentage inhibition of TNFα in murine macrophages by compounds 6 and 7 of the invention.

HMC synergy with cisplatin was assessed either in combination over 5 days exposure or in sequence (HMC→cisplatin) against the MM200 melanoma cell line. It was difficult to assess for synergistic toxicity using a change in IC50 as a measure of synergy due to HMC toxicity as monotherapy (Table 8). 3D analysis of the data reveals that only additive toxicity was apparent using the 5-day combination protocol (FIG. 11). Evidence of synergy using the HMC-cisplatin combination was further assessed using the HMC→cisplatin sequence (24 hr exposure to each compound in sequence) against the melanoma cell line MM200. Using change in IC50 to assess for synergy it was noted that HMC at concentrations of 2 μM markedly chemosensitised the MM200 cells to cisplatin by >1000 fold (Table 8). HMC induced chemosensitisation of MM200 cells to cisplatin was confirmed using 3D analysis of the data (FIG. 11B). These data demonstrate that HMC is able to chemosensitise cancer cells, in this case melanoma, to cisplatin.

TABLE 8

Comparative assessment of synergy between HMC and the cisplatin against the Mel-RM melanoma cell line. Average IC50 data for each agent when assessed as a monotherapy or in combination are shown

| DRUG | TREATMENT (IC50 μM) | | | | |
|---|---|---|---|---|---|
| | Combined | Change Factor | 24 hr | HMC first | Change Factor |
| cisplatin | 8.82 | — | 6.32 | — | — |
| HMC | 0.72 | — | 20.64 | — | — |
| HMC 10 μM | 1.00E−06 | HMC effect | — | 1.28E−05 | >10000 |
| HMC 5 μM | 1.00E−06 | HMC effect | — | 2.71E−05 | >10000 |
| HMC 2 μM | 1.00E−06 | HMC effect | — | 1.00E−06 | >10000 |
| HMC 1 μM | 0.45 | HMC effect | — | 8.29 | −1.31 |

3.7.2 HMC Combination with Gemcitabine Against the Mel-RM Melanoma Cells

HMC synergy with gemcitabine was assessed either in combination over 5 days exposure or in sequence (HMC→gemcitabine) against the Mel-RM melanoma cell line. It was difficult to assess for synergistic toxicity using a change in IC50 as a measure of synergy due to HMC toxicity as monotherapy (Table 9). 3D analysis of the data reveals that 5-day combination protocol did not elicit synergistic toxicity against the Mel-RM cell line. Evidence of synergy using the HMC-gemcitabine combination was further assessed using the HMC→gemcitabine sequence (24 hr exposure to each compound in sequence) against the melanoma cell line Mel-RM. Using change in IC50 to assess for synergy it was noted that HMC at concentrations of 2 and 1 μM markedly chemosensitised the Mel-RM cells to gemcitabine by >1000 fold. HMC-induced chemosensitisation of Mel-RM cells to gemcitabine was confirmed using 3D analysis of the data. These data demonstrate that HMC is able to chemosesnsitise cancer cells to gemcitabine.

TABLE 9

Comparative assessment of synergy between HMC and gemcitabine against the Mel-RM melanoma cell line. Average IC50 data for each agent when assessed as a monotherapy or in combination are shown.

| DRUG | TREATMENT (IC50 μM) | | | | |
|---|---|---|---|---|---|
| | Combined | Change Factor | 24 Hr | HMC first | Change Factor |
| HMC | 0.51 | — | 27.79 | — | — |
| HMC 1 μM | 1.00E−06 | ?HMC effect | — | 1.76E−03 | >1000 |
| HMC 2 μM | 1.00E−06 | ?HMC effect | — | 1.00E−06 | >1000 |
| Gemcitabine | 3.88E−03 | — | 4.67E−03 | — | — |
| HMC | 0.51 | — | 27.79 | — | — |
| HMC 1 μM | 1.00E−06 | ?HMC effect | — | 1.00E−06 | >1000 |
| HMC 2 μM | 1.00E−06 | ?HMC effect | — | 3.89E−05 | >100 |

3.7.3. HMC Combination with Paclitaxel Against the 4405 Melanoma Cell Line

HMC synergy with paclitaxel was assessed either in combination over 5 days exposure or in sequence (HMC→paclitaxel) against the 4405 melanoma cell line. It was difficult to assess for synergistic toxicity using a change in IC50 as a measure of synergy due to HMC toxicity as monotherapy (Table 10). A 30 fold reduction in IC50 was noted in the combination experiment when compared to the paclitaxel monotherapy. However, 3D analysis of the data revealed that the 5-day combination protocol did not elicit synergistic toxicity against the 4405 cell line. Evidence of synergy using the HMC-paclitaxel combination was further assessed using the HMC→paclitaxel sequence (24 hr exposure to each compound in sequence) against the melanoma cell line 4405. Using change in IC50 to assess for synergy it was noted that HMC at concentrations of 2 μM markedly chemosensitised the 4405 cells to paclitaxel by >1000 fold (Table 10). HMC-induced chemosensitisation of MM200 cells to paclitaxel was confirmed using 3D analysis of the data. These data demonstrate that HMC is able to chemosensitise cancer cells to paclitaxel.

TABLE 10

Comparative assessment of synergy between HMC and paclitaxel against the 4405 melanoma cell line. Average IC50 data for each agent when assessed as a monotherapy or in combination are shown.

| DRUG | TREATMENT (IC50 μM) | | | | |
|---|---|---|---|---|---|
| | Combined | Change Factor | 24 hr | HMC first | Change Factor |
| HMC 1 μM | 0.006 | 1.00 | — | 0.03 | −4.44 |
| HMC 2 μM | 1.00E−06 | 5964.400 | — | 0.01 | −1.035 |
| Paclitaxel | 1.25E−07 | — | 5.84E−04 | — | — |
| HMC | 1.26 | — | 55.50 | — | — |
| HMC 1 μM | 4.12E−09 | 30.36 | — | 5.31E−05 | 11.00 |
| HMC 2 μM | 3.91E−10 | ?HMC effect | — | 5.48E−09 | 106633.75 |

3.7.4. HMC Combination with Topotecan Against the MM200 Melanoma Cell Line

HMC synergy with topotecan was assessed either in combination over 5 days exposure or in sequence (HMC→topotecan) against the MM200 melanoma cell line. It was difficult to assess for synergistic toxicity using a change in IC50 as a measure of synergy due to HMC toxicity as monotherapy (Table 8). 30 analysis of the data confirmed that the 5-day combination protocol did not elicit synergistic toxicity against the MM200 cell line. Evidence of synergy using the HMC-gemcitabine combination was further assessed using the HMC→topotecan sequence (24 hr exposure to each compound in sequence) against the melanoma cell line MM200. Using change in IC50 to assess for synergy it was noted that HMC at a concentration of 2 μM markedly chemosensitised the MM200 cells to topotecan by >1000 fold (Table 11). HMC-induced chemosensitisation of MM200 cells to topotecan was confirmed using 3D analysis of the data. These data demonstrate that HMC is able to chemosensitise cancer cells to topotecan. From the 3D analysis the optimum combination of HMC and topotecan against the MM200 melanoma cell line would appear to be 2 μM HMC and between 1 and 0.1 μM topotecan.

TABLE 11

Comparative assessment of synergy between HMC and topotecan against the MM200 melanoma cell line. Average IC50 data for each agent when assessed as a monotherapy or in combination are shown.

| DRUG | TREATMENT (IC50 μM) | | | | |
|---|---|---|---|---|---|
| | Combined | Change Factor | 24 hr | HMC first | Change Factor |
| HMC 1 μM | 0.115 | −14.145 | — | 0.009 | 9.304 |
| HMC 2 μM | 1.00E−06 | ?HMC effect | — | 7.85E−05 | >1000 |
| Topotecan | 0.095 | — | 2.216 | — | — |
| HMC | 0.702 | — | 17.952 | — | — |
| HMC 1 μM | 0.000 | ?HMC effect | — | 0.044 | 50.656 |
| HMC 2 μM | 1.00E−06 | ?HCM effect | — | 1.00E−06 | >10000.00 |

3.7.5. HMC Combination with Camptothecin Against the Mel-RM Melanoma Cell Line HMC synergy with doxorubicin was assessed either in combination over 5 days exposure or in sequence (HMC→doxorubicin) against the Mel-RM melanoma cell line. It was difficult to assess for synergistic toxicity using a change in IC50 as a measure of synergy due to HMC toxicity as monotherapy (Table 12). 3D analysis of the data confirmed that the 5-day combination protocol did not elicit synergistic toxicity against the Mel-RM cell line, indeed evidence of antagonism was noted. Evidence of synergy using the HMC-doxorubicin combination was further assessed using the HMC→doxorubicin sequence protocol (24 hr exposure to each compound in sequence) against the melanoma cell line Mel-RM. Using change in IC50 to assess for synergy it was noted that HMC at a concentration of 2 μM chemosensitised the Mel-RM cells to camptothecin by ~12 fold (Table 12). 3D analysis of the data, however, reveal a marked degree of synergy between HMC and doxorubicin against Mel-RM cells. These data demonstrate that HMC is able to chemosensitise cancer cells to paclitaxel. From the 3D analysis the optimum combination of HMC and camptothecin against the MM200 melanoma cell line would appear to be 2 μM HMC and between 1 and 0.1 μM doxorubicin.

TABLE 12

Comparative assessment of synergy between HMC and doxorubicin against the Mel-RM melanoma cell line. Average IC50 data for each agent when assessed as a monotherapy or in combination are shown.

| DRUG | TREATMENT (IC50 μM) | | | | |
|---|---|---|---|---|---|
| | Combined | Change Factor | 24 hr | HMC first | Change Factor |
| Doxorubicin | 0.19 | — | 0.100 | — | — |
| HMC | 0.54 | — | 50.515 | — | — |
| HMC 1 μM | 0.40 | −2.06 | — | 0.062 | 1.62 |
| HMC 2 μM | 0.18 | ?HMC effect | — | 8.16E−03 | 12.22 |

3.8 Inhibition of TNFα in Murine Macrophages (RAW 264.7) by Compounds 4, 6 & 7

The mouse macrophage cell line RAW 264.7 was cultured in DMEM supplemented with FCS, 2 mM glutamine and 50 U/ml penicillin/streptomycin. Subconfluent cells were detached from the flask by gentle scraping and 24-well plates seeded at $5 \times 10^5$ cells per well and allowed to adhere for 1 hr. Cells were treated with either test agent (in 0.025% DMSO) or vehicle alone, 1 hr prior to the addition of 50 ng/ml LPS. After incubation for 16 hrs, culture media was collected and stored at −80° C. for TNFα. measurement using an enzyme immunometric assay (Becton Dickinson).

Compound 6 and compound 7 of the present invention were tested and the results are shown in FIG. 12, which indicated that the compounds tested inhibit TNFα. in murine macrophages in a dose dependent manner over the concentration ranges tested.

The raw data for compounds 6, 7 and additionally compound 4 is shown in Table 13 below.

TABLE 13

Inhibition of TNFα in murine macrophages by compounds 4, 6 and 7

| Concentration (μM) | Compound 6 | Compound 7 | Compound 4 |
|---|---|---|---|
| 10 | −48.7 | −26.2 | −6.1 |
| 1 | −13.0 | −25.4 | −11.9 |
| 0.1 | −10.4 | −1.4 | −6.3 |
| 0.001 | 1.0 | 19.2 | −14.3 |
| 0.01 | — | — | −11.3 |

3.9 Assessment of HHC as a Chemosensitiser

HHC was screened as chemosensitiser against a panel cell lines representative of a range cancer indications using a panel of cytotoxics commonly used in the treatment of cancer. It has emerged that HHC has an ability to strongly chemosensitise cancer cell lines from different pathologies to gemcitabine (ovarian, prostate, breast and pancreatic cancers, and glioma) (Table 14). Strong synergy has been noted using HHC:cisplatin against ovarian and prostate cancer, mild synergy against colorectal cancer cell lines and synergy was not observed in pancreatic cancer and glioma. Moderate synergy has been noted using the HHC:paclitaxel combination against breast and colorectal cancer, and melanoma cell lines. Equivocal synergy data using the HHC:paclitaxel combination has been noted against ovarian cancer and glioma cell lines and there was no evidence of synergy against prostate and pancreatic cancer cell lines. Data has revealed that HHC is able to strongly chemosensitise the MM96L melanoma cell line to cisplatin, carboplatin and decarbazine (Table 7).

TABLE 14

Assessment of HHC as a chemosensitiser using a panel of cancer cell lines and standard cytotoxics

| Drug | Cancer Indication | | | | | |
|---|---|---|---|---|---|---|
| | Ovarian CP70 | Prostate PCS | Breast MDA-468 | Melanoma MM96L | Glioma HTB-138 | Pancreatic HPAC |
| Cisplatin | SSSSS | SSSSS | — | SSSSS | n.o. | n.o. |
| | — | SSSSS | — | — | n.o. | — |
| | — | — | — | — | — | — |
| Gemcitabine | SSSSS | SSSSS | SSSSS | — | SSSSS | SSSSS |
| | — | — | — | — | SSSSS | — |
| Paclitaxel | n.o. | n.o. | MS | — | MS | n.o. |
| | MS | — | — | — | n.o. | — |
| | — | — | — | — | n.o. | — |
| Carboplatin | — | .. | — | SSSSS | — | — |
| Dacarbazine | — | — | — | SSSSS | — | — |

Key:
SSSSS = Synergy
MS = moderate synergy
n.o. = not observed
* = not tested

3.10. Efficacy of DHE, HMC and HHC Against Selected Melanoma Cell Lines

In comparison with DHE, both HMC and HHC showed excellent anti-cancer activity against a range of melanoma cell lines. HHC was the most efficacious agent against all melanoma cell lines tested to date having sub 1 μM IC50 values (Table 15).

The invention has been described herein, with reference to certain preferred embodiments, in order to enable the reader to practice the invention without undue experimentation.

TABLE 15

Comparison of DHE, HMC and HHC efficacy against melanoma monotherapy

| | Melanoma coining (IC58 μM) | | | | | | |
|---|---|---|---|---|---|---|---|
| Analogue | MM200 | A2058 | IgR3 | RM | 4405 | MM96L | SKMe128 |
| DHE | 4.77 ± 4 | NT | NT | NT | NT | 4.76 | 4.40 |
| HMC | 1.13 ± 0.52 | 1.42 ± 0.48 | 0.51 ± 0.08 | 1.4 ± 1.6 | 1.46 ± 0.18 | 1.31 ± 0.38 | 0.68 ± 0.16 |
| HHC | 0.66 ± 0.28 | 0.34 | 0.20 | 0.39 ± 0.28 | 0.50 | 0.2 ± 0.09 | 0.36 ± 0.34 |

4.0 Effect on Murine Macrophages (RAW 264.7) Stimulated with LPS

The mouse macrophage cell line RAW 264.7 was cultured in DMEM supplemented with foetal calf serum (FCS), 2 mM glutamine and 50 U/ml penicillin/streptomycin. Subconfluent cells were detached from the flask by gentle scraping and 24-well plates seeded at 5×10⁵ cells per well and allowed to adhere for 1 hr. Cells were then treated either test compound at a concentration of 10 μM (in 0.025% DMSO) or vehicle alone, and incubated for 1 hr. LPS 50 ng/ml (LPS-Sigma-Aldrich) was then added. After incubation for 16 hrs, culture media was collected and stored at −80° C. for ecosanoid measurements using enzyme immunometric assays (PGE$_2$ and TXB$_2$—Cayman Chemical).

TABLE 16

Percentage change in eicosanoid synthesis after incubating test compound at 10 μM compared with incubation with vehicle alone. Positive values indicate enhanced synthesis; negative values indicate inhibition of synthesis and consequently suggest anti-inflammatory activity.

| Compound | PGE$_2$ | TXB$_2$ |
|---|---|---|
| 1 | −33.8 | 0 |
| 2 | −12.6 | 16 |
| 6 | −37.7 | −16.4 |
| 11 | 27.2 | 51.4 |

The invention has been described herein, with reference to certain preferred embodiments, in order to enable the reader to practice the invention without undue experimentation. However, a person having ordinary skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The entire disclosures of all applications, patents and publications, cited herein, if any, are hereby incorporated by reference.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

The reference to any prior art in this specification is not, and should not be taken as, an acknowledgment or any form of suggestion that that prior art forms part of the common general knowledge in the field of endeavour.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SELECTED REFERENCE ARTICLES

Constantinou A I, Mehta R, Husband A. 2003 Phenoxodiol, a novel isoflavone derivative, inhibits dimethylbenz[a]anthracene (DMBA)-induced mammary carcinogenesis in female Sprague-Dawley rats. Eur J Cancer. 39, 1012-8.

Constantinou AI, Husband A. 2002 Phenoxodiol (2H-1-benzopyran-7-0,1,3-(4-hydroxyphenyl)), a novel isoflavone derivative, inhibits DNA topoisomcrase II by stabilizing the cleavable complex. Anticancer Res. 22, 2581-5.

Gamble, J R., Xia, P., Hahn, C., Drew, J., Drogemuller, C., Carter, C., Walker, C., Brown, D M., Vadas, M A. 2003 Phenoxodiol, a derivative of plant flavanoids, shows potent anti-tumour and anti-angiogenic properties. Nature Medicine. Submitted.

Hersey, P and Zhang, X. D. 2001 How melanoma cells evade Trail-induced apoptosis. Nature reviews, Cancer, 1, 142-150.

Kamsteeg, M., Rutherford, T., Sapi, E., Hanczaruk, B., Shahabi, S., Flick, M., Brown, D. M and Mor, G. 2003 Phenoxodiol—an isoflvone analogue—induces apoptosis in chemo-resistant ovarian cancer cells. Oncogene; 22, 2611-20.

O'Dwyer P J, Moyer J D, Suffness M, Harrison S D Jr, Cysyk R, Hamilton T C, Plowman J. 1994 Antitumor activity and biochemical effects of aphidicolin glycinate (NSC 303812) alone and in combination with cisplatin in vivo. Cancer Res. 54, 724-9

Todorov P T, Field W N, Tisdale M J 1999 Role of a proteolysis-inducing factor (PIF) in cachexia induced by a human melanoma (G361). Br J Cancer. 80,1734-7.

Bellisarii, F. L., S. Gallina, et al. (2001). "Tumor necrosis factor-alpha and cardiovascular diseases." Italian Heart Journal: Official Journal of the Italian Federation of Cardiology, 2(6): 408-17.

Szlosarek, P. W. and F. R. Balkwill (2003). "Tumour necrosis factor alpha: a potential target for the therapy of solid tumours." Lancet Oncol 4(9): 565-73.

Nakata E, Hunter N, Mason K, Fan Z, Ang K K, Milas L. 2004 C225 antiepidermal growth factor receptor antibody enhances the efficacy of docetaxel chemoradiotherapy. Int J Radiat Oncol Biol Phys. 59(4):1163-73.

What is claimed is:

1. A method of treating cancer, the method comprising administering to a subject in need thereof a compound of the formula (I-a):

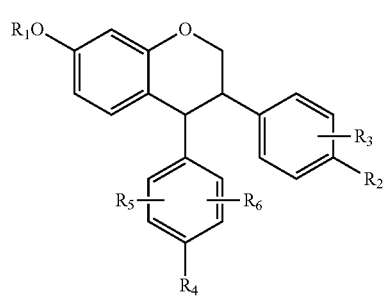

(I-a)

wherein $R_1$ is alkyl;

$R_2$ and $R_3$ are independently hydrogen, hydroxy, alkoxy, halo, or alkyl, with the exception that $R_2$ and $R_3$ are not both hydrogen; and $R_4$, $R_5$ and $R_6$ are independently hydrogen, hydroxy, alkoxy, or alkyl;

or a pharmaceutically acceptable salt thereof.

2. The method of claim 1, wherein the cancer is of epithelial, mesenchymal, or neural origin.

3. The method of claim 2, wherein the cancer is ovarian cancer, breast cancer, pancreatic cancer, or melanoma.

4. The method of claim 1, wherein administering the compound of formula (I-a) results in the cancer being sensitized to one or more chemotherapeutic agent or radiotherapy, and the method further comprises administering to the subject a chemotherapeutic agent or radiotherapy to which the cancer has been sensitized.

5. The method of claim 4, wherein the chemotherapeutic agent is selected from the group consisting of cisplatin, carboplatin, paclitaxel, gemcitabine, doxorubicin, decarbazine, or topotecan.

6. A method of sensitizing a cancer cell, the method comprising contacting the cancer cell with a compound of formula (I-a):

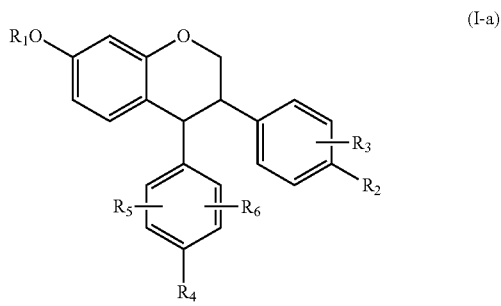

(I-a)

wherein $R_1$ is alkyl;

$R_2$ and $R_3$ are independently hydrogen, hydroxy, alkoxy, halo or alkyl, with the exception that $R_2$ and $R_3$ are not both hydrogen; and $R_4$, $R_5$ and $R_6$ are independently hydrogen, hydroxy, alkoxy, or alkyl;

or a pharmaceutically acceptable salt thereof.

7. The method of claim 6, wherein the cancer is of epithelial, mesenchymal, or neural origin.

8. The method of claim 7, wherein the cancer is ovarian cancer, breast cancer, pancreatic cancer, or melanoma.

9. The method of claim of 6, wherein the method of sensitizing comprises sensitizing the cancer cell to a chemotherapeutic agent to which, prior to the method of sensitizing, the cancer cell is not sensitive or is poorly sensitive.

10. The method of claim 6, wherein the method of sensitizing comprises sensitizing the cancer cell to radiotherapy to which, prior to the method of sensitizing, the cancer cell is not sensitive or is poorly sensitive.

* * * * *